US008003855B2

(12) United States Patent
Somerville et al.

(10) Patent No.: US 8,003,855 B2
(45) Date of Patent: **\*Aug. 23, 2011**

(54) PRODUCTION OF HYDROXYLATED FATTY ACIDS IN GENETICALLY MODIFIED PLANTS

(75) Inventors: Chris Somerville, Portola Valley, CA (US); Pierre Broun, Burlingame, CA (US); Frank van de Loo, Weston (AU); Sekhar S. Boddupalli, Manchester, MI (US)

(73) Assignees: Carnegie Institution of Washington, Washington, DC (US); Monsanto Company, Inc., St. Louis, MO (US)

( * ) Notice: Subject to any disclaimer, the term of this patent is extended or adjusted under 35 U.S.C. 154(b) by 494 days.

This patent is subject to a terminal disclaimer.

(21) Appl. No.: 11/905,067

(22) Filed: Sep. 27, 2007

(65) Prior Publication Data

US 2009/0070902 A1    Mar. 12, 2009

Related U.S. Application Data

(60) Division of application No. 11/058,746, filed on Feb. 16, 2005, now abandoned, which is a division of application No. 09/885,189, filed on Jun. 21, 2001, now Pat. No. 6,936,728, which is a continuation of application No. 08/597,313, filed on Feb. 6, 1996, now Pat. No. 6,310,194, which is a continuation-in-part of application No. 08/530,862, filed on Sep. 20, 1995, now Pat. No. 6,291,742, which is a continuation-in-part of application No. 08/320,982, filed on Oct. 11, 1994, now Pat. No. 5,801,026, which is a continuation-in-part of application No. 08/314,596, filed on Sep. 26, 1994, now Pat. No. 5,668,292.

(51) Int. Cl.
*A01H 5/00* (2006.01)
*C11B 1/00* (2006.01)

(52) U.S. Cl. ............................................. 800/306; 554/9
(58) Field of Classification Search .................. None
See application file for complete search history.

(56) References Cited

U.S. PATENT DOCUMENTS

| | | | |
|---|---|---|---|
| 5,057,419 A | 10/1991 | Martin et al. | 435/134 |
| 5,443,974 A | 8/1995 | Hitz et al. | 800/264 |
| 5,475,099 A | 12/1995 | Knauf et al. | 536/23.6 |
| 5,487,991 A | 1/1996 | Vandekerckhove et al. | 435/69.1 |
| 5,530,186 A | 6/1996 | Hitz et al. | 800/264 |
| 5,530,194 A | 6/1996 | Knauf et al. | 800/264 |
| 5,543,576 A | 8/1996 | van Ooijen et al. | 800/317.3 |
| 5,552,306 A | 9/1996 | Thomas et al. | 435/134 |
| 5,559,223 A | 9/1996 | Falco et al. | 800/278 |
| 5,589,619 A | 12/1996 | Chappell et al. | 800/278 |
| 5,668,292 A | 9/1997 | Somerville et al. | 800/205 |
| 5,801,026 A | 9/1998 | Somerville et al. | 435/172.3 |
| 5,846,784 A | 12/1998 | Hitz | 435/91.2 |
| 5,850,026 A | 12/1998 | DeBonte et al. | 800/281 |
| 5,965,793 A | 10/1999 | Broun et al. | 800/287 |
| 6,291,742 B1 | 9/2001 | Somerville et al. | 800/281 |
| 6,310,194 B1 | 10/2001 | Somerville et al. | 536/23.6 |
| 6,372,965 B1 | 4/2002 | Lightner et al. | 800/298 |
| 6,872,872 B1 | 3/2005 | Lightner et al. | 800/298 |
| 6,936,728 B2 * | 8/2005 | Somerville et al. | 554/8 |

FOREIGN PATENT DOCUMENTS

| | | |
|---|---|---|
| AU | 718512 | 4/2000 |
| AU | 723161 | 11/2000 |
| WO | WO 93/11245 A | 6/1993 |
| WO | WO 94/11513 | 5/1994 |
| WO | WO 94/11516 A | 5/1994 |
| WO | WO 94/18337 A | 8/1994 |
| WO | WO 96/10075 A | 4/1996 |
| WO | WO 97/21340 A | 6/1997 |
| WO | WO 97/22711 | 6/1997 |
| WO | WO 97/30582 | 8/1997 |
| WO | WO 98/06735 | 2/1998 |
| WO | WO 98/46762 | 10/1998 |
| WO | WO 99/53073 | 10/1999 |

OTHER PUBLICATIONS

Altschul et al, "Basic local alignment search tool" J. Mol. Biol., 215:403-410 (1990).
Arondel et al, "Map-based cloning of a gene controlling omega-3 fatty acid desaturation in Arabidopsis" Science, 258:1353-1355 (1992).
Atsmon et al, "Castor" in *Oil Crops of the World*, Robbelen, G., Downey, K.R., and Ashri, A., eds. McGraw-Hill, New York pp. 438-447 (1989).
Badami et al., "Structure and Occurrence of Unusual Fatty Acids in Minor Seed Oils" Prog. Lipid Res. 19:119 and 132-136 (1981).
Bafor et al, "Ricinoleic acid biosynthesis and triacylglycerol assembly in microsomal preparations from developing castor-bean" Biochem., 280:507-514 (1991).
Battey et al, "A comparison of the metabolic fate of fatty acids of different chain lengths in developing oilseeds" Plant Physiol., 90:835-840 (1989). Bechtold et al, "In Planta Agrobacterium mediated gene transfer by infiltration of adult *Arabidopsis thaliana* plants" C.R. Acad. Sci. Paris, 316:1194-1199 (1993).
Beltz et al, "Isolation of multigene families and determination of homologies by filter hybridization methods" Methods in Enzymology, 100:266-285 (1983).
Benfy et al., "The Cauliflower Mosaic Virus 35S promoter: combinational regulation of transcription in plants" Science 250: 959-966 (1990).
Bray et al, "Expression of the .beta.-conglycinin in seeds of transgenic plants." Planta, 172:364-370 (1987).
Broun et al., "A bifunctional oleate 12-hydroxylase: desaturase from *Lesquerella fendleri*" Plant J. 13(2):201-210 (1998).
Broun et al., "Accumulation of ricinoleic, lesquerolic, and densipolic acids in seeds of transgenic *Arabidopsis* plants that express a fatty acyl hydroxylase cDNA from castor bean" Plant Physiol. 113: 933-942 (1997).

(Continued)

*Primary Examiner* — Elizabeth McElwain
(74) *Attorney, Agent, or Firm* — Morgan, Lewis & Bockius LLP

(57) ABSTRACT

This invention relates to plant fatty acyl hydroxylases. Methods to use conserved amino acid or nucleotide sequences to obtain plant fatty acyl hydroxylases are described. Also described is the use of cDNA clones encoding a plant hydroxylase to produce a family of hydroxylated fatty acids in transgenic plants. In addition, the use of genes encoding fatty acid hydroxylases or desaturases to alter the level of lipid fatty acid unsaturation in transgenic plants is described.

8 Claims, 17 Drawing Sheets

OTHER PUBLICATIONS

Broun et al., "Catalytic Plasticity of Fatty Acid Modification Enzymes Underlying Chemical Diversity of Plant Lipids" Science 282:1315-1317 (1998).

Browse et al, "Glycerolipid synthesis: biochemistry and regulation" Ann. Rev. Plant Physiol. Plant Mol. Biol., 42:467-506 (1991).

Cahoon et al., "Redesign of soluble fatty acid desaturase from plants for altered substrate specificity and double bond position" Proc. Natl.Acad. Sci. USA 94: 4872-4877 (1997).

Canvin, D.T., Formation of oil in the seed of Ricinus communis L., Can. J. Biochem. Physiol., 41:1879-1885 (1963).

Carlson et al., "Analysis of Oil and Meat from Lesquerella fendleri Seed" Am. Oil. Chem. Soc. 67:495-498 (1990).

Database EMBL, EMBL No. U22378, Somerville C.R.: "An oleate 12-hydroxylase from Ricinus communis L. is a fatty acyl saturase homolog." Apr. 1995.

Database MBL Nucleotide and Protein Sequences, XP002120959, Lycopersicum esculentum ( Apr. 16, 1995).

De Luca, "Molecular characterization of secondary metabolis pathways" Biotech News and Information 5:225N-229N (1997).

Dierks et al., "Glu-320 and Asp-323 are determinants of the CYP4A1 hydroxylation regiospecificity and resistance to inactivation by 1-aminobenzotriazole" Biochem. 37: 1839-1847 (1998).

Ditta et al, "Broad host range DNA cloning system for gram-negative bacteria: Construction of a gene bank of Phizobium meliloti" Proc. Natl. Acad. Sci. USA, 77:7347-7351 (1980).

Fessner, W. D., "Are Paradigms Changing in Favor of Biocatalysis?"Adv. Synth. Catal. 345:649-650 (2003).

Fox et al, "Stearoyl-acyl carrier protein $\Delta^9$ desaturase from Ricinus communis is a diiron-oxo protein" Proc. Natl. Acad. Sci., 90:2486-2490 (1993).

Galliard et al, "Fat metabolism in higher plants XXX. Enzymatic synthesis of ricinoleic acid by a microsomal preparation from developing Ricinus communis seeds" J. Biol. Chem., 241:5806-5812 (1966).

Gould et al, "Use of the DNA polymerase chain reaction for homology probing" Proc. Natl. Acad. Sci. USA, 86:1934-1938 (1989).

Greenwood et al, "Seed development in Ricinus communis (castor bean) I. Descriptive morphology" Can. J. Bot., 60:1751-1760 (1982).

Griffiths et al., "Delta6 and Delta12-Desaturase Activities and Phosphatidic Acid Formation in Microsomal Preparations from the Developing Cotyledons of Common Borage" Biochemical Journal 252:641-647 (1988).

Gunstone et al, The Lipid Handbook, Chapman and Hall, London, Chapters 1.9, pp. 19-20 and 3.3.5, pp. 57-58 (1986).

Howling et al, "The specificity of fatty acid desaturases and hydroxylases: the dehydrogenation and hydroxylation of monoenoic acids" Biochim. Biophys. Acta, 260:10-19 (1972).

Huynh al, "Constructing and screening cDNA libraries in .lambda. gt10 and .lambda.gt11" in DNA Cloning, vol. 1: A Practical Approach, (ed) D.M. Glover, IRL Press, Washington, D.C., pp. 49 (1985).

Iba et al, "A gene encoding a chloroplast omega-3 fatty acid desaturase complements alterations in fatty acid desaturation and chloroplast copy number of the fad7 mutant of Arabidopsis thaliana" J. Biol. Chem., 268:24099-24105 (1993).

International Search Report for PCT App. No. PCT/US99/08400, mailed Dec. 15, 1999.

James et al, "The biosynthesis of ricinoleic acid" Biochem. J., 95:448-452 (1965).

Jones et al, "Effective vectors for transformation, expression of heterologous genes, and assaying transposon excision in transgenic plants" Transgenic Res., 1:285-297 (1992).

Kearns et al, "The role of cytochrome b5 in delta desaturation of oleic acid by microsomes of safflower (Carthamus tinctorius L.)" Arch. Biochem. Biophys., 284:431-436 (1991).

Kim et al., "A 20 nucleotide upstream element is essential for the nopaline synthase (nos) promoter activity" Plant Mol. Biol. 24:105-117 (1994).

Knuzton et al, "Modification of Brassica seed oil by antisense expression of a stearoyl-acyl carrier protein desaturase gene" Proc. Natl. Acad. Sci. USA, 89:2624-2628 (1992).

Kok et al, "The Pseudomonas oleovorans alkane hydroxylase gene: sequence and expression" J. Biol. Chem., 264:5435-5441 (1989).

Konez et al, "The promoter of $T_L$-DNA gene 5 controls the tissue-specific expression of chimetic tenes carried by a novel type of Agrobacterium binary vector" Mol. Gen. Genet., 204:383-396 (1986).

Kren et al, "Occurrence of ricinoleic acid in submerged cultures of various Claviceps sp.", Experentia, 41:1476-1477 (1985).

Kridl et al., "Control of Plant Gene Expression" CRC Press, pp. 481-498 (1993).

Matzke et al., "How and why do plants inactivate homologous (Trans) genes?" Plant Physiol. 107: 679-685 (1995).

McKeon et al., Plant Physiol. 105: 64 (1994).

Miguel et al, "Arabidopsis Mutants Deficient in Polyunsaturated Fatty Acid Synthesis" J. Biol. Chem., 267:1502-1509 (1992).

Moreau et al, "Recent studies of the enzymic synthesis of ricinoleic acid by developing castor beans" Plant Physiol., 67:672-676 (1981).

Morris et al, Biochem. J., "The biosynthesis of ricinoleic acid by Claviceps purpurea" 100:29c-30c (1966).

Morris, "The Mechanism of ricinoleic acid biosynthesis in Ricinus communis seeds" Biochem. Biophys. Res. Commun., 29:311-315 (1967).

Morris, L.J., "Mechanisms and stereochemistry in fatty acid metabolism" Biochem. J., 118:681-693 (1970).

Murray et al, "Rapid isolation of high molecular weight plant DNA" Nucl. Acids Res., 8:4321-4325 (1980).

Napoli et al., "Introduction of a Chimeric Chalcone Synthase Gene into Petunia Results in Reversible Co-Suppression of Homologous Genes in trans" The Plant Cell 2:278-289 (1990).

Newman et al, "DST sequences, highly conserved among plant SAUR genes, target reporter transcripts for rapid decay in tobacco" Plant Cell, 5:701-714 (1993).

Ohlrogge et al., "Design of new plant products: Engineering of fatty acid metabolism" Plant Physiol. 104: 821-826 (1994).

Okuley et al., "Arabidopsis FAD2 Gene Encodes the Enzyme that is Essential for Polyunsaturated Lipid Synthesis" Plant Cell 6:147-158 (1994).

Ooms et al, "Octopine Ti-plasmid deletion mutants of Agrobacterium tumefaciens with emphasis on the right side of the T-region" Plasmid, 7:15-29 (1982).

Panaccione et al, "Characterization of two divergent B-tubulia genes from Colletotrichum graminicola" Gene, 86:163-170 (1990).

Post-Beittenmiller et al., "Regulation of plant lipid biosynthesis: an example of developmental regulation superimposed on a ubiquitous pathway" In DPS Verma, ed, Control of Plant Gene Expression. CRC Press, Boca Raton, FL, pp. 157-174 (1993).

Prasad et al, "Phospholipids of palash (Butea monosperma), papaya (Carica papaya), jangli badam (Sterculla foetida), coriander (Coriandrum sativum), and carrot (Daucus carota) seeds" J. Am. Oil Chem. Soc., 64:1424-1427 (1987).

Puissant et al, "An improvement of the single-step method of RNA isolation by acid guanidinium thiocyanate-phenol-chloroform extraction" BioTechniques, 8:148-149 (1990).

Sambrook et al, Molecular Cloning: a Laboratory Manual, 2n ed., Cold Spring Harbor Laboratory Press (1989).

Schmidt et al, "New in vivo and in vitro evidence for lipid-linked desaturation in plants" in Biochemistry and Molecular Biology of Membrane and Storage Lipids of Plants, eds. N. Murata and C.R. Somerville, American Society of Plant Physiologists, pp. 40-49 (1993).

Shanklin et al., "Eight histidine residues are catalyticaly essential in a membrane-associated iron enzyme, stearoyl-CoA desaturase, and are conserved in alkane hydroxylase and xylene monooxygenase" Biochem. 33: 12787-12794 (1994).

Smith et al, "Evidence for cytochorme $b_5$ as an electron donor in ricinoleic acid biosynthesis in microsomal preparations from developing castor bean (Ricinus communis L.)" Biochem. J., 287:141-144 (1992).

Smith, C.R., "Unusual seed oils and their fatty acids" in Fatty Acids, Pryde E.H., Ed., American Oil Chemists' Society, Champaign, 2nd ed., pp. 29-47 (1985).

Suzuki et al, "Primary structure of xylene monooxygenase: similarities to and differences from the alkane hydoxylation system" J. Bacteriol., 173:1690-1695 (1991).

Thiede et al, "Construction and Sequence of cDNA for Rat Liver Stearyl Coenzyme A Desaturase" J. Biol. Chem., 261:13230-13235 (1986).

Topfer et al., "Modification of plant lipid synthesis" Science 268: 681-686 (1995).

Truan et al., "Thr268 in substrate binding and catalysis in P4350 BM-3" Arch. Biochem. Biophys. 349(1): 53-64 (1998).

van de Loo et al, "A plastid omega-3 desaturase from castor (*Ricinus communis* L.)" Plant Physiol., 105:443-444 (1994).

van de Loo et al, "Lipid Metabolism in Plants" T.S. Moore Jr., Ed., CRC Press, Boca Raton, pp. 91-126 (1993).

van de Loo et al., "An Oleate 12-hydroxylase from *Ricinus comunis* L. is a fatty acyl saturase homolog" Proc. Natl. Sci. USA 92(15):6743-7 (1995).

von Heijne, "Signal Sequences" J. Mol. Biol., 184:99-105 (1985).

Yadav et al, "Cloning of higher plant 03 fatty acid desaturases" Plant Physiol., 103:467-476 (1993).

Yang et al., "Directed Evolution Approach to a Structural Genomics Project: Rv2002 from *Mycobacterium tuberclosis*" Proc. Natl. Acad. Sci. USA 100:455-460 (2003).

\* cited by examiner

Ion #1: Mass 187
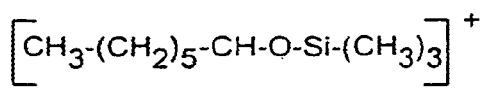
Ion #2: Mass 299
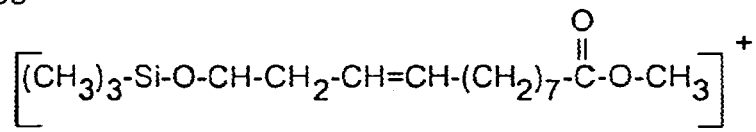
Ion #3: Mass 270 (characteristic rearrangement ion)
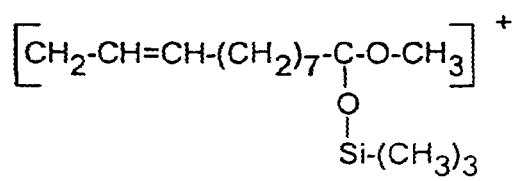
Ion #4: Mass 185 (desaturated analog of Ion #1)
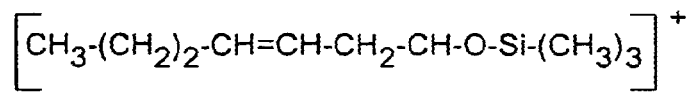
Ion #5: Mass 298 (elongated analog of Ion #3)
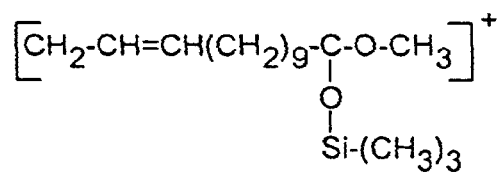
Ion #6: Mass 327 (elongated analog of ion
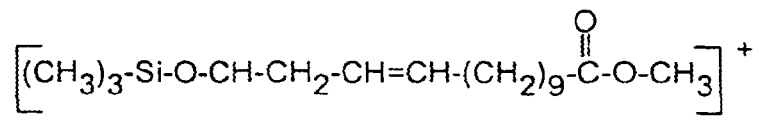
Figure 2

Figure 4A  Mass spectrum of peak 10 from figure 3B
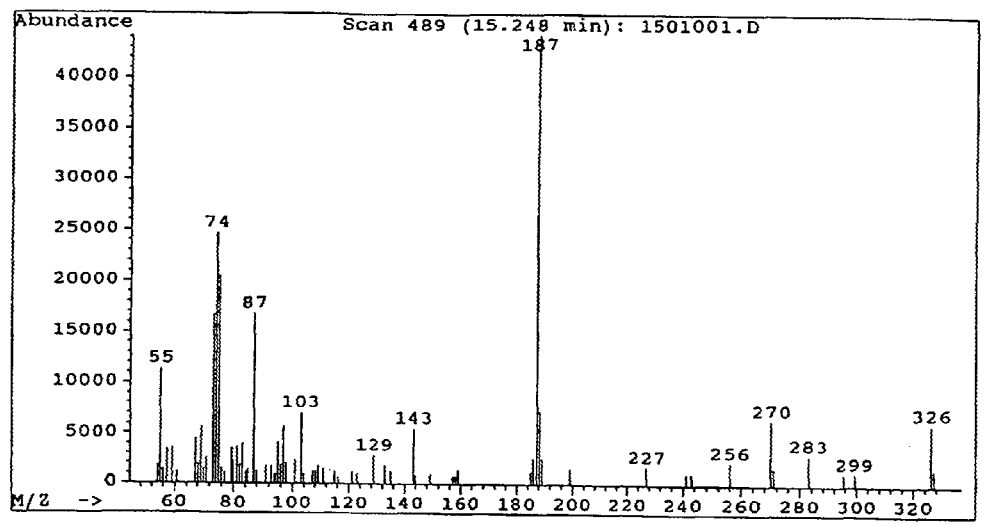
Figure 4B  Mass spectrum of peak 11 from figure 3B
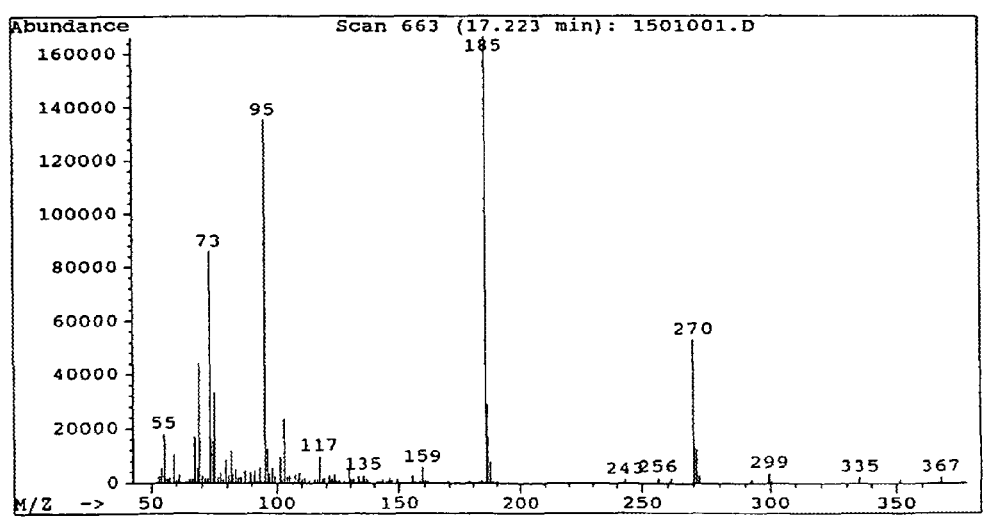

Figure 4C  Mass spectrum of peak 12 from figure 3B
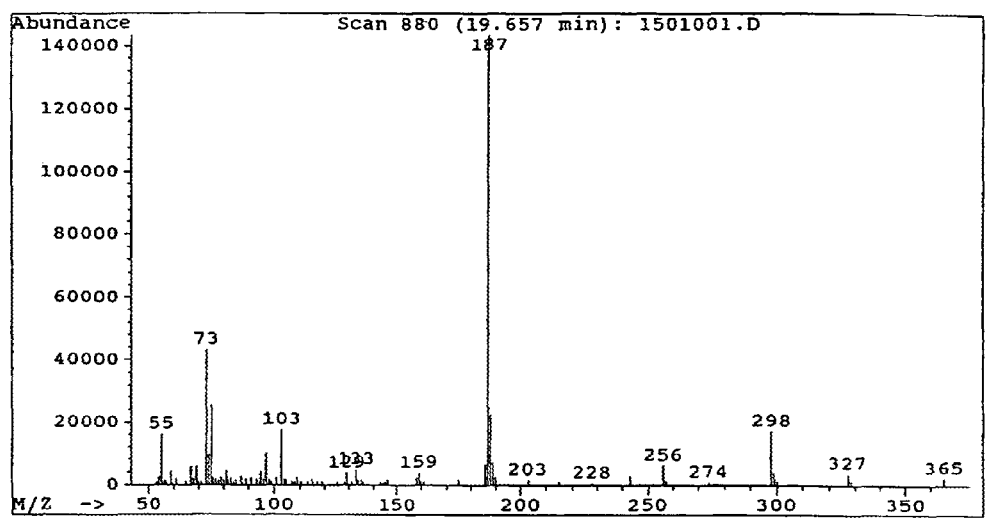
Figure 4D  Mass spectrum of peak 13 from figure 3B
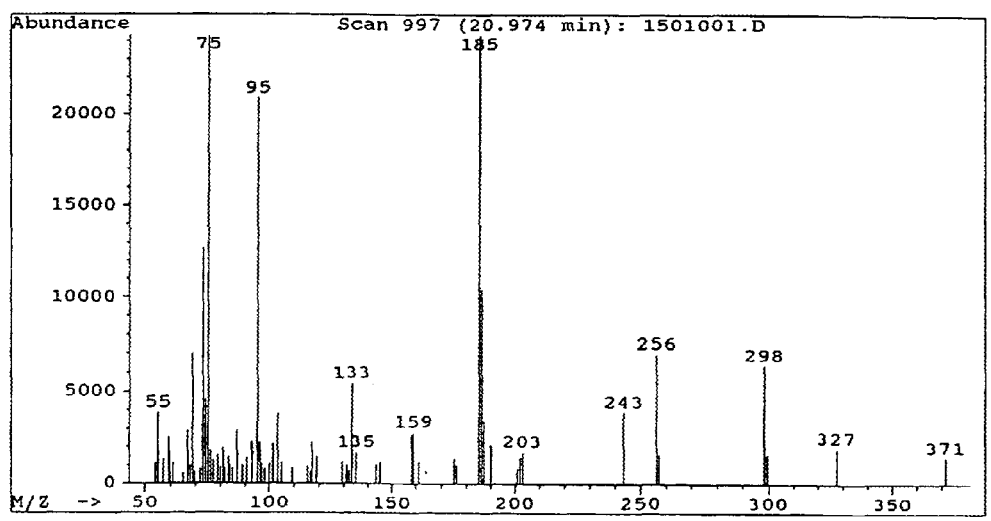

```
         10         20         30         40         50         60
TATTGGCACC GGCGGCACCA TTCCAACAAT GGATCCCTAG AAAAAGATGA AGTCTTTGTC
         70         80         90        100        110        120
CCACCTAAGA AAGCTGCAGT CANATGGTAT GTCAAATACC TCAACAACCC TCTTGGACGC
        130        140        150        160        170        180
ATTCTGGTGT TAACAGTTCA GTTTATCCTC GGGTGGCCTT TGTATCTAGC CTTTAATGTA
        190        200        210        220        230        240
TCAGGTAGAC CTTATGATGG TTTCGCTTCA CATTTCTTCC CTCATGCACC TATCTTTAAG
        250        260        270        280        290        300
GACCGTGAAC GTCTCCAGAT ATACATCTCA GATGCTGGTA TTCTAGCTGT CTGTTATGGT
        310        320        330        340        350        360
CTTTACCGTT ACGCTGCTTC ACAAGGATTG ACTGCTATGA TCTGCGTCTA CGGAGTACCG
        370        380        390        400        410        420
CTTTTGATAG TGAACTTTTT CCTTGTCTTG GTCACTTTCT TGCAGCACAC TCATCCTTCA
        430        440        450        460        470        480
TTACCTCACT ATGATTCAAC CGAGTGGGAA TGGATTAGAG GAGCTTTGGT TACGGTAGAC
        490        500        510        520        530        540
AGAGACTATG GAATCTTGAA CAAGGTGTTT CACAACATAA CAGACACCCA CGTAGCACAC
        550
CAC
```

Figure 5

```
         10         20         30         40         50         60
TATAGGCACC GGAGGCACCA TTCCAACACA GGATCCCTCG AAAGAGATGA AGTATTTGTC
         70         80         90        100        110        120
CCAAAGCAGA AATCCGCAAT CAAGTGGTAC GGCGAATACC TCAACAACCC TCCTGGTCGC
        130        140        150        160        170        180
ATCATGATGT TAACTGTCCA GTTCGTCCTC GGATGGCCCT TGTACTTAGC CTTCAACGTT
        190        200        210        220        230        240
TCTGGCAGAC CCTACAATGG TTTCGCTTCC CATTTCTTCC CCAATGCTCC TATCTACAAC
        250        260        270        280        290        300
GACCGTGAAC GCCTCCAGAT TTACATCTCT GATGCTGGTA TTCTAGCCGT CTGTTATGGT
        310        320        330        340        350        360
CTTTACCGTT ACGCTGTTGC ACAAGGACTA GCCTCAATGA TCTGTCTAAA CGGAGTTCCG
        370        380        390        400        410        420
CTTCTGATAG TTAACTTTTT CCTCGTCTTG ATCACTTACT TACAACACAC TCACCCTGCG
        430        440        450        460        470        480
TTGCCTCACT ATGATTCATC AGAGTGGGAT TGGCTTAGAG GAGCTTTAGC TACTGTAGAC
        490        500        510        520        530        540
AGAGACTATG GAATCTTGAA CAAGGTGTTC CATAACATCA CAGACACCCA CGTCGCACAC
        550
CACT
```

Figure 6

```
AT GAA GCT TTA TAA GAA GTT AGT TTT CTC TGG TGA CAG AGA AAT TNT          47
GTC AAT TGG TAG TGA CAG TTG AAG CAA CAG GAA CAA CAA GGA TGG TTG          95
GTG NTG ATG CTG ATG TGG TGA TGT GTT ATT CAT CAA ATA CTA AAT ACT         143
ACA TTA CTT GTT GCT GCC TAC TTC TCC TAT TTC CTC CGC CAC CCA TTT         191
TGG ACC CAC GAN CCT TCC ATT TAA ACC CTC TCT CGT GCT ATT CAC CAG         239
AAG AGA AGC CAA GAG AGA GAG AGA GAG AAT GTT CTG AGG ATC ATT GTC         287
TTC TTC ATC GTT ATT AAC GTA AGT TTT TTT TGA CCA CTC ATA TCT AAA         335
ATC TAG TAC ATG CAA TAG ATT AAT GAC TGT TCC TTC TTT TGA TAT TTT         383
                              Met Gly Ala Gly Gly Arg Ile Met Val Thr    10
CAG CTT CTT GAA TTC AAG ATG GGT GCT GGT GGA AGA ATA ATG GTT ACC         431
Pro Ser Ser Lys Lys Ser Glu Thr Glu Ala Leu Lys Arg Gly Pro Cys          26
CCC TCT TCC AAG AAA TCA GAA ACT GAA GCC CTA AAA CGT GGA CCA TGT         479
Glu Lys Pro Pro Phe Thr Val Lys Asp Leu Lys Lys Ala Ile Pro Gln          42
GAG AAA CCA CCA TTC ACT GTT AAA GAT CTG AAG AAA GCA ATC CCA CAG         527
His Cys Phe Lys Arg Ser Ile Pro Arg Ser Phe Ser Tyr Leu Leu Thr          58
CAT TGT TTC AAG CGC TCT ATC CCT CGT TCT TTC TCC TAC CTT CTC ACA         575
Asp Ile Thr Leu Val Ser Cys Phe Tyr Tyr Val Ala Thr Asn Tyr Phe          74
GAT ATC ACT TTA GTT TCT TGC TTC TAC TAC GTT GCC ACA AAT TAC TTC         623
Ser Leu Leu Pro Gln Pro Leu Ser Thr Tyr Leu Ala Trp Pro Leu Tyr          90
TCT CTT CTT CCT CAG CCT CTC TCT ACT TAC CTA GCT TGG CCT CTC TAT         671
Trp Val Cys Gln Gly Cys Val Leu Thr Gly Ile Trp Val Ile Gly His         106
TGG GTA TGT CAA GGC TGT GTC TTA ACC GGT ATC TGG GTC ATT GGC CAT         719
Glu Cys Gly His His Ala Phe Ser Asp Tyr Gln Trp Val Asp Asp Thr         122
GAA TGT GGT CAC CAT GCA TTC AGT GAC TAT CAA TGG GTA GAT GAC ACT         767
Val Gly Phe Ile Phe His Ser Phe Leu Leu Val Pro Tyr Phe Ser Trp         138
GTT GGT TTT ATC TTC CAT TCC TTC CTT CTC GTC CCT TAC TTC TCC TGG         815
Lys Tyr Ser His Arg Arg His His Ser Asn Asn Gly Ser Leu Glu Lys         154
AAA TAC AGT CAT CGT CGT CAC CAT TCC AAC AAT GGA TCT CTC GAG AAA         863
Asp Glu Val Phe Val Pro Pro Lys Lys Ala Ala Val Lys Trp Tyr Val         170
GAT GAA GTC TTT GTC CCA CCG AAG AAA GCT GCA GTC AAA TGG TAT GTT         911
Lys Tyr Leu Asn Asn Pro Leu Gly Arg Ile Leu Val Leu Thr Val Gln         186
AAA TAC CTC AAC AAC CCT CTT GGA CGC ATT CTG GTG TTA ACA GTT CAG         959
```

Figure 8A

```
Phe Ile Leu Gly Trp Pro Leu Tyr Leu Ala Phe Asn Val Ser Gly Arg    202
TTT ATC CTC GGG TGG CCT TTG TAT CTA GCC TTT AAT GTA TCA GGT AGA   1007

Pro Tyr Asp Gly Phe Ala Ser His Phe Phe Pro His Ala Pro Ile Phe    218
CCT TAT GAT GGT TTC GCT TCA CAT TTC TTC CCT CAT GCA CCT ATC TTT   1055

Lys Asp Arg Glu Arg Leu Gln Ile Tyr Ile Ser Asp Ala Gly Ile Leu    234
AAA GAC CGA GAA CGC CTC CAG ATA TAC ATC TCA GAT GCT GGT ATT CTA   1103

Ala Val Cys Tyr Gly Leu Tyr Arg Tyr Ala Ala Ser Gln Gly Leu Thr    250
GCT GTC TGT TAT GGT CTT TAC CGT TAC GCT GCT TCA CAA GGA TTG ACT   1151

Ala Met Ile Cys Val Tyr Gly Val Pro Leu Leu Ile Val Asn Phe Phe    266
GCT ATG ATC TGC GTC TAT GGA GTA CCG CTT TTG ATA GTG AAC TTT TTC   1199

Leu Val Leu Val Thr Phe Leu Gln His Thr His Pro Ser Leu Pro His    282
CTT GTC TTG GTA ACT TTC TTG CAG CAC ACT CAT CCT TCG TTA CCT CAT   1247

Tyr Asp Ser Thr Glu Trp Glu Trp Ile Arg Gly Ala Leu Val Thr Val    298
TAT GAT TCA ACC GAG TGG GAA TGG ATT AGA GGA GCT TTG GTT ACG GTA   1295

Asp Arg Asp Tyr Gly Ile Leu Asn Lys Val Phe His Asn Ile Thr Asp    314
GAC AGA GAC TAT GGA ATA TTG AAC AAG GTG TTC CAT AAC ATA ACA GAC   1343

Thr His Val Ala His His Leu Phe Ala Thr Ile Pro His Tyr Asn Ala    330
ACA CAT GTG GCT CAT CAT CTC TTT GCA ACT ATA CCG CAT TAT AAC GCA   1391

Met Glu Ala Thr Glu Ala Ile Lys Pro Ile Leu Gly Asp Tyr Tyr His    346
ATG GAA GCT ACA GAG GCG ATA AAG CCA ATA CTT GGT GAT TAC TAC CAC   1439

Phe Asp Gly Thr Pro Trp Tyr Val Ala Met Tyr Arg Glu Ala Lys Glu    362
TTC GAT GGA ACA CCG TGG TAT GTG GCC ATG TAT AGG GAA GCA AAG GAG   1487

Cys Leu Tyr Val Glu Pro Asp Thr Glu Arg Gly Lys Lys Gly Val Tyr    378
TGT CTC TAT GTA GAA CCG GAT ACG GAA CGT GGG AAG AAA GGT GTC TAC   1535

Tyr Tyr Asn Asn Lys Leu                                            384
TAT TAC AAC AAT AAG TTA TGA GGC TGA TAG GGC GAG AGA AGT GCA ATT   1583

ATC AAT CTT CAT TTC CAT GTT TTA GGT GTC TTG TTT AAG AAG CTA TGC   1631

TTT GTT TCA ATA ATC TCA GAG TCC ATN TAG TTG TGT TCT GGT GCA TTT   1679

TGC CTA GTT ATG TGG TGT CGG AAG TTA GTG TTC AAA CTG CTT CCT GCT   1727

GTG CTG CCC AGT GAA GAA CAA GTT TAC GTG TTT AAA ATA CTC GGA ACG   1775

AAT TGA CCA CAA NAT ATC CAA AAC CGG CTA TCC GAA TTC CAT ATC CGA   1823

AAA CCG GAT ATC CAA ATT TCC AGA GTA CTT AG                        1855
```

Figure 8B

```
              10         20         30         40         50
LFFAH12    1 MGAGGRIM-- --VTPSSKKS --ETEALKRG PCEKPPFTVK DLKKAIPQHC   50
FAH12      1 MGGGGRMSTV ITSNNSEKKG --GSSHLKRA PHTKPPFTLG DLKRAIPPHC   50
ATFAD2     1 MGAGGRMP-- --VPTSSKKS --ETDTTKRV PCEKPPFSVG DLKKAIPPHC   50
BNFAD2     1 MGAGGRMQ-- --VSPPSKKS --ETDNIKRV PCETPPFTVG ELKKAIPPHC   50
GMFAD2-1   1 MGLA-KETTM GGRGRVAKVE VQGKKPLSRV PNTKPPFTVG QLKKAIPPHC   50
GMFAD2-2   1 MGAGGR---- TDVPPANRKS --EVDPLKRV PFEKPQFSLS QIKKAIPPHC   50
ZMFAD2     1 MGAGGRMTEK EREKQEQLAR ATGGAAMQRS PVEKPPFTLG QIKKAIPPHC   50
RCFAD2     1 ---------- ---------- ---------- ---------- ----------   50
              60         70         80         90        100
LFFAH12   51 FKRSIPRSFS YLLTDITLVS CFYYVATNYF SLLPQPLSTY LAWPLYWVCQ  100
FAH12     51 FERSFVRSFS YVAYDVCLSF LFYSIATNFF PYISSPLS-Y VAWLVYWLFQ  100
ATFAD2    51 FKRSIPRSFS YLISDIIIAS CFYYVATNYF SLLPQPLS-Y LAWPLYWACQ  100
BNFAD2    51 FKRSIPRSFS HLIWDIIIAS CFYYVATTYF PLLPNPLS-Y FAWPLYWACQ  100
GMFAD2-1  51 FQRSLLTSFS YVVYDLSFAF IFY-IATTYF HLLPQPFS-L IAWPIYWVLQ  100
GMFAD2-2  51 FQRSVLRSFS YVVYDLTIAF CLYYVATHYF HLLPGPLS-F RGMAIYWAVQ  100
ZMFAD2    51 FERSVLKSFS YVVHDLVIAA ALLYFALAII PALPSPLR-Y AAWPLYWIAQ  100
RCFAD2    51 ---------- ---------- ---------- ---------- ----------  100
             110        120        130        140        150
LFFAH12  101 GCVLTGIWVI GHECGHHAFS DYQWVDDTVG FIFHSFLLVP YFSWKYSHRR  150
FAH12    101 GCILTGLWVI GHECGHHAFS EYQLADDIVG LIVHSALLVP YFSWKYSHRR  150
ATFAD2   101 GCVLTGIWVI AHECGHHAFS DYQWLDDTVG LIFHSFLLVP YFSWKYSHRR  150
BNFAD2   101 GCVLTGVWVI AHECGHAAFS DYQWLDDTVG LIFHSFLLVP YFSWKYSHRR  150
GMFAD2-1 101 GCLLTGVWVI AHECGHHAFS KYQWVDDVVG LTLHSTLLVP YFSWKISHRR  150
GMFAD2-2 101 GCILTGVWVI AHECGHHAFS DYQLLDDIVG LILHSALLVP YFSWKYSHRR  150
ZMFAD2   101 G--------- -------AFS DYSLLDDVVG LVLHSSLMVP YFSWKYSHRR  150
RCFAD2   101 -------WVM AHDCGHHAFS DYQLLDDVVG LILHSCLLVP YFSWKHSHRR  150
             160        170        180        190        200
LFFAH12  151 HHSNNGSLEK DEVFVPPKKA AVKWYVKYL- NNPLGRILVL TVQFILGWPL  200
FAH12    151 HHSNIGSLER DEVFVPKQKS KISWYSKYS- NNPPGRVLTL AATLLLGWPL  200
ATFAD2   151 HHSNTGSLER DEVFVPKQKS AIKWYGKYL- NNPLGRIMML TVQFVLGWPL  200
BNFAD2   151 HHSNTGSLER DEVFVPR-RS QTSSGTAST- STTFGRTVML TVQFTLGWPL  200
GMFAD2-1 151 HHSNTGSLDR DEVFVPKPKS KVAWFSKYL- NNPLGRAVSL LVTLTIGWPM  200
GMFAD2-2 151 HHSNTGSLER DEVFVPKQKS CIKWYSKYL- NNPPGRVLTL AVTLTLGWPL  200
ZMFAD2   151 HHSNTGSLER DEVFVPKKKE ALPWYTPYVY NNPVGRVVHI VVQLTLGWPL  200
RCFAD2   151 HHSNTGSLER DEVFVPKKKS SIRWYSKYL- NNPPGRIMTI AVTLSLGWPL  200
             210        220        230        240        250
LFFAH12  201 YLAFNVSGRP YDG-FASHFF PHAPIFKDRE RLQIYISDAG ILAVCYGLYR  250
FAH12    201 YLAFNVSGRP YDR-FACHYD PYGPIFSERE RLQIYIADLG IFATTFVLYQ  250
ATFAD2   201 YLAFNVSGRP YDG-FACHFF PNAPIYNDRE RLQIYLSDAG ILAVCFGLYR  250
BNFAD2   201 YLAFNVSGRP YDGGFACHFH PNAPIYNDRE RLQIYISDAG ILAVCYGLLP  250
GMFAD2-1 201 YLAFNVSGRP YDS-FASHYH PYAPIYSNRE RLLIYVSDVA LFSVTYSLYR  250
GMFAD2-2 201 YLALNVSGRP YDR-FACHYD PYGPIYSDRE RLQIYISDAG VLAVVYGLFR  250
ZMFAD2   201 YLATNASGRP YPR-FACHFD PYGPIYNDRE RAQIFVSDAG VVAVAFGLYK  250
RCFAD2   201 YLAFNVSGRP YDR-FACHYD PYGPIYNDRE RIEIFISDAG VLAVTFGLYQ  250
```

Figure 9A

```
              260        270        280        290        300
LFFAH12  251 YAASQGLTAM ICVYGVPLLI VNFFLVLVTF LQHTHPSLPH YDSTEWEWIR  300
FAH12    251 ATMAKGLAWV MRIYGVPLLI VNCFLVMITY LQHTHPAIPR YGSSEWDWLR  300
ATFAD2   251 YAAAQGMASM ICLYGVPLLI VNAFLVLITY LQHTHPSLPH YDSSEWDWLR  300
BNFAD2   251 YAAVQGVASM VCFLRVPLLI VNGFLVLITY LQHTHPSLPH YDSSEWDWLR  300
GMFAD2-1 251 VATLKGLVWL LCVYGVPLLI VNGFLVTITY LQHTHFALPH YDSSEWDWLK  300
GMFAD2-2 251 LAMAKGLAWV VCVYGVPLLV VNGFLVLITF LQHTHPALPH YTSSEWDWLR  300
ZMFAD2   251 LAAAFGVWWV VRVYAVPLLI VNAWLVLITY LQHTHPSLPH YDSSEWDWLR  300
RCFAD2   251 LAIAKGLAWV VCVYGVPLLV VNSFLVLITF LQHTHPALPH YDSSEWDWLR  300

310        320        330        340        350
LFFAH12  301 GALVTVDRDY GILNKVFHNI TDTHVAHHLF ATIPHYNAME ATEAIKPILG  350
FAH12    301 GAMVTVDRDY GVLNKVFHNI ADTHVAHHLF ATVPHYHAME ATKAIKPIMG  350
ATFAD2   301 GALATVDRDY GILNKVFHNI TDTHVAHHLF STMPHYNAME ATKAIKPILG  350
BNFAD2   301 GALATVDRDY GILNQGFHNI TDTHEAHHLF STMPHYHAME ATKAIKPILG  350
GMFAD2-1 301 GALATMDRDY GILNKVFHHI TDTHVAHHLF STMPHYNAME ATNAIKPILG  350
GMFAD2-2 301 GALATVDRDY GILNKVFHNI TDTHVAHHLF STMPHYHAME ATKAIKPILG  350
ZMFAD2   301 GALATMDRDY GILNRVFHNI TDTHVAHHLF STMPHYHAME ATKAIRPILG  350
RCFAD2   301 GALATVDRDY GILNKVFHNI TDTQVAHHLF ---------- ----------  350
              360        370        380        390        400
LFFAH12  351 DYYHFDGTPW YVAMYREAKE CLYVEPDTER GKKGVYYYNN K-L.......  400
FAH12    351 EYYRYDGTPF YKALWREAKE CLFVEPDEGA PTQGVFWYRN KY-.......  400
ATFAD2   351 DYYQFDGTPW YVAMYREAKE CIYVEPDREG DKKGVYWYNN K-L.......  400
BNFAD2   351 EYYQFDGTPW VKAMWREAKE CIYVEPDRQG EKKGVFWYNN KL*.......  400
GMFAD2-1 351 EYYQFDDTPF YKALWREARE CLYVEPDEGT SEKGVYWYRN KY-.......  400
GMFAD2-2 351 EYYRFDETPF VKAMWREARE CIYVEPDQST ESKGVFWYNN KL-.......  400
ZMFAD2   351 DYYHFDPTPV AKATWREAGE CIYVEPE--- DRKGVFWYNK KF*.......  400
```

Figure 9B

Plasmid name: pSLJ44026
Plasmid size: 25.70 kb
Constructed by: Jonathon Jones
Construction date: 1992
Comments/References: Transgenic Research 1,285-297 (1992)

SEQUENCE LISTING

<160> NUMBER OF SEQ ID NOS: 15

<210> SEQ ID NO 1
<211> LENGTH: 543
<212> TYPE: DNA
<213> ORGANISM: Artificial sequence
<220> FEATURE:
<223> OTHER INFORMATION: Nucleotide sequence of pLesq2
<220> FEATURE:
<221> NAME/KEY: misc_feature

```
<222> LOCATION: (83)..(83)
<223> OTHER INFORMATION: n is a, c, g, or t

<400> SEQUENCE: 1
tattggcacc ggcggcacca ttccaacaat ggatccctag aaaaagatga agtctttgtc      60
ccacctaaga aagctgcagt canatggtat gtcaaatacc tcaacaaccc tcttggacgc     120
attctggtgt taacagttca gtttatcctc gggtggcctt tgtatctagc ctttaatgta     180
tcaggtagac cttatgatgg tttcgcttca catttcttcc ctcatgcacc tatctttaag     240
gaccgtgaac gtctccagat atacatctca gatgctggta ttctagctgt ctgttatggt     300
ctttaccgtt acgctgcttc acaaggattg actgctatga tctgcgtcta cggagtaccg     360
cttttgatag tgaactttt ccttgtcttg gtcactttct gcagcacac tcatccttca      420 ttacctcact atgattcaac cgagtgggaa tggattagag gagctttggt tacggtagac     480
agagactatg gaatcttgaa caaggtgttt cacaacataa cagacaccca cgtagcacac     540
cac                                                                  543

<210> SEQ ID NO 2
<211> LENGTH: 544
<212> TYPE: DNA
<213> ORGANISM: Artificial sequence
<220> FEATURE:
<223> OTHER INFORMATION: Nucleotide sequence of pLesq3

<400> SEQUENCE: 2
tataggcacc ggaggcacca ttccaacaca ggatccctcg aaagagatga agtatttgtc      60
ccaaagcaga aatccgcaat caagtggtac ggcgaatacc tcaacaaccc tcctggtcgc     120
atcatgatgt taactgtcca gttcgtcctc ggatggccct tgtacttagc cttcaacgtt     180
tctggcagac cctacaatgg tttcgcttcc catttcttcc ccaatgctcc tatctacaac     240
gaccgtgaac gcctccagat ttacatctct gatgctggta ttctagccgt ctgttatggt     300
ctttaccgtt acgctgttgc acaaggacta gcctcaatga tctgtctaaa cggagttccg     360
cttctgatag ttaactttt cctcgtcttg atcacttact acaacacac tcaccctgcg      420 ttgcctcact atgattcatc agagtgggat tggcttagag gagctttagc tactgtagac     480
agagactatg gaatcttgaa caaggtgttc cataacatca cagacaccca cgtcgcacac     540
cact                                                                 544

<210> SEQ ID NO 3
<211> LENGTH: 1855
<212> TYPE: DNA
<213> ORGANISM: Artificial sequence
<220> FEATURE:
<223> OTHER INFORMATION: Nucleotide sequence of genomic clone encoding
      pLesq-HYD
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (1658)..(1658)
<223> OTHER INFORMATION: n is a, c, g, or t
<220> FEATURE:
```

<221> NAME/KEY: misc_feature
<222> LOCATION: (1788)..(1788)
<223> OTHER INFORMATION: n is a, c, g, or t

<400> SEQUENCE: 3

```
atgaagcttt ataagaagtt agttttctct ggtgacagag aaattntgtc aattggtagt      60
gacagttgaa gcaacaggaa caacaaggat ggttggtgnt gatgctgatg tggtgatgtg     120
ttattcatca atactaaat actacattac ttgttgctgc ctacttctcc tatttcctcc      180
gccacccatt ttggacccac ganccttcca tttaaaccct ctctcgtgct attcaccaga     240
agagaagcca agagagagag agagagaatg ttctgaggat cattgtcttc ttcatcgtta     300
ttaacgtaag ttttttttga ccactcatat ctaaaatcta gtacatgcaa tagattaatg     360
actgttcctt cttttgatat tttcagcttc ttgaattcaa gatgggtgct ggtggaagaa     420
taatggttac cccctcttcc aagaaatcag aaactgaagc cctaaaacgt ggaccatgtg     480
agaaaccacc attcactgtt aaagatctga agaaagcaat cccacagcat tgtttcaagc     540
gctctatccc tcgttctttc tcctaccttc tcacagatat cactttagtt tcttgcttct     600
actacgttgc cacaaattac ttctctcttc ttcctcagcc tctctctact tacctagctt     660
ggcctctcta ttgggtatgt caaggctgtg tcttaaccgg tatctgggtc attggccatg     720
aatgtggtca ccatgcattc agtgactatc aatgggtaga tgacactgtt ggttttatct     780
tccattcctt ccttctcgtc ccttacttct cctggaaata cagtcatcgt cgtcaccatt     840
ccaacaatgg atctctcgag aaagatgaag tctttgtccc accgaagaaa gctgcagtca     900
aatggtatgt taaataccct aacaaccctc ttggacgcat tctggtgtta acagttcagt     960
ttatcctcgg gtggccttg tatctagcct ttaatgtatc aggtagacct tatgatggtt    1020
tcgcttcaca tttcttccct catgcaccta tctttaaaga ccgagaacgc ctccagatat    1080
acatctcaga tgctggtatt ctagctgtct gttatggtct ttaccgttac gctgcttcac    1140
aaggattgac tgctatgatc tgcgtctatg gagtaccgct tttgatagtg aacttttcc      1200
ttgtcttggt aactttcttg cagcacactc atccttcgtt acctcattat gattcaaccg     1260
agtgggaatg gattagagga gctttggtta cggtagacag agactatgga atattgaaca     1320
aggtgttcca taacataaca gacacacatg tggctcatca tctctttgca actataccgc     1380
attataacgc aatggaagct acagaggcga taaagccaat acttggtgat tactaccact     1440
tcgatggaac accgtggtat gtggccatgt atagggaagc aaaggagtgt ctctatgtag     1500
aaccggatac ggaacgtggg aagaaaggtg tctactatta caacaataag ttatgaggct     1560
gatagggcga gagaagtgca attatcaatc ttcattttcca tgttttaggt gtcttgttta    1620
agaagctatg ctttgtttca atastctcag agtccatnta gttgtgttct ggtgcatttt     1680
gcctagttat gtggtgtcgg aagttagtgt tcaaactgct tcctgctgtg ctgcccagtg     1740
aagaacaagt ttacgtgttt aaaatactcg gaacgaattg accacaanat atccaaaacc     1800
ggctatccga attccatatc cgaaaaccgg atatccaaat ttccagagta cttag          1855
```

<210> SEQ ID NO 4
<211> LENGTH: 384
<212> TYPE: PRT
<213> ORGANISM: Lesquerella fendleri

<400> SEQUENCE: 4

```
Met Gly Ala Gly Gly Arg Ile Met Val Thr Pro Ser Ser Lys Lys Ser
1               5                   10                  15

Glu Thr Glu Ala Leu Lys Arg Gly Pro Cys Glu Lys Pro Pro Phe Thr
```

```
                20                  25                  30
Val Lys Asp Leu Lys Lys Ala Ile Pro Gln His Cys Phe Lys Arg Ser
            35                  40                  45

Ile Pro Arg Ser Phe Ser Tyr Leu Leu Thr Asp Ile Thr Leu Val Ser
        50                  55                  60

Cys Phe Tyr Tyr Val Ala Thr Asn Tyr Phe Ser Leu Leu Pro Gln Pro
65                  70                  75                  80

Leu Ser Thr Tyr Leu Ala Trp Pro Leu Tyr Trp Val Cys Gln Gly Cys
                85                  90                  95

Val Leu Thr Gly Ile Trp Val Ile Gly His Glu Cys Gly His His Ala
            100                 105                 110

Phe Ser Asp Tyr Gln Trp Val Asp Asp Thr Val Gly Phe Ile Phe His
            115                 120                 125

Ser Phe Leu Leu Val Pro Tyr Phe Ser Trp Lys Tyr Ser His Arg Arg
        130                 135                 140

His His Ser Asn Asn Gly Ser Leu Glu Lys Asp Glu Val Phe Val Pro
145                 150                 155                 160

Pro Lys Lys Ala Ala Val Lys Trp Tyr Val Lys Tyr Leu Asn Asn Pro
                165                 170                 175

Leu Gly Arg Ile Leu Val Leu Thr Val Gln Phe Ile Leu Gly Trp Pro
            180                 185                 190

Leu Tyr Leu Ala Phe Asn Val Ser Gly Arg Pro Tyr Asp Gly Phe Ala
        195                 200                 205

Ser His Phe Phe Pro His Ala Pro Ile Phe Lys Asp Arg Glu Arg Leu
    210                 215                 220

Gln Ile Tyr Ile Ser Asp Ala Gly Ile Leu Ala Val Cys Tyr Gly Leu
225                 230                 235                 240

Tyr Arg Tyr Ala Ala Ser Gln Gly Leu Thr Ala Met Ile Cys Val Tyr
                245                 250                 255

Gly Val Pro Leu Leu Ile Val Asn Phe Phe Leu Val Leu Val Thr Phe
            260                 265                 270

Leu Gln His Thr His Pro Ser Leu Pro His Tyr Asp Ser Thr Glu Trp
        275                 280                 285

Glu Trp Ile Arg Gly Ala Leu Val Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ala Thr Ile Pro His Tyr Asn Ala Met Glu Ala Thr Glu Ala
                325                 330                 335

Ile Lys Pro Ile Leu Gly Asp Tyr Tyr His Phe Asp Gly Thr Pro Trp
            340                 345                 350

Tyr Val Ala Met Tyr Arg Glu Ala Lys Glu Cys Leu Tyr Val Glu Pro
        355                 360                 365

Asp Thr Glu Arg Gly Lys Lys Val Tyr Tyr Asn Asn Lys Leu
    370                 375                 380

<210> SEQ ID NO 5
<211> LENGTH: 387
<212> TYPE: PRT
<213> ORGANISM: Ricinus communis

<400> SEQUENCE: 5

Met Gly Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
```

```
            20                  25                  30
Pro Pro Phe Thr Leu Gly Asp Leu Lys Arg Ala Ile Pro Pro His Cys
            35                  40                  45

Phe Glu Arg Ser Phe Val Arg Ser Phe Ser Tyr Val Ala Tyr Asp Val
        50                  55                  60

Cys Leu Ser Phe Leu Phe Tyr Ser Ile Ala Thr Asn Phe Phe Pro Tyr
65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
        210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
290                 295                 300

Tyr Gly Val Leu Asn Lys Val Phe His Asn Ile Ala Asp Thr His Val
305                 310                 315                 320

Ala His His Leu Phe Ala Thr Val Pro His Tyr His Ala Met Glu Ala
                325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
        370                 375                 380

Asn Lys Tyr
385

<210> SEQ ID NO 6
<211> LENGTH: 383
<212> TYPE: PRT
<213> ORGANISM: Arabidopsis thaliana

<400> SEQUENCE: 6

Met Gly Ala Gly Gly Arg Met Pro Val Pro Thr Ser Ser Lys Lys Ser
```

```
            1               5                  10                 15
Glu Thr Asp Thr Thr Lys Arg Val Pro Cys Glu Lys Pro Pro Phe Ser
            20                 25                 30

Val Gly Asp Leu Lys Lys Ala Ile Pro Pro His Cys Phe Lys Arg Ser
            35                 40                 45

Ile Pro Arg Ser Phe Ser Tyr Leu Ile Ser Asp Ile Ile Ala Ser
        50                 55                 60

Cys Phe Tyr Tyr Val Ala Thr Asn Tyr Phe Ser Leu Leu Pro Gln Pro
65                  70                 75                 80

Leu Ser Tyr Leu Ala Trp Pro Leu Tyr Trp Ala Cys Gln Gly Cys Val
                85                 90                 95

Leu Thr Gly Ile Trp Val Ile Ala His Glu Cys Gly His His Ala Phe
                100                105                110

Ser Asp Tyr Gln Trp Leu Asp Asp Thr Val Gly Leu Ile Phe His Ser
            115                120                125

Phe Leu Leu Val Pro Tyr Phe Ser Trp Lys Tyr Ser His Arg Arg His
            130                135                140

His Ser Asn Thr Gly Ser Leu Glu Arg Asp Glu Val Phe Val Pro Lys
145                 150                155                160

Gln Lys Ser Ala Ile Lys Trp Tyr Gly Lys Tyr Leu Asn Asn Pro Leu
                165                170                175

Gly Arg Ile Met Met Leu Thr Val Gln Phe Val Leu Gly Trp Pro Leu
                180                185                190

Tyr Leu Ala Phe Asn Val Ser Gly Arg Pro Tyr Asp Gly Phe Ala Cys
                195                200                205

His Phe Phe Pro Asn Ala Pro Ile Tyr Asn Asp Arg Glu Arg Leu Gln
            210                215                220

Ile Tyr Leu Ser Asp Ala Gly Ile Leu Ala Val Cys Phe Gly Leu Tyr
225                 230                235                240

Arg Tyr Ala Ala Ala Gln Gly Met Ala Ser Met Ile Cys Leu Tyr Gly
                245                250                255

Val Pro Leu Leu Ile Val Asn Ala Phe Leu Val Leu Ile Thr Tyr Leu
                260                265                270

Gln His Thr His Pro Ser Leu Pro His Tyr Asp Ser Ser Glu Trp Asp
            275                280                285

Trp Leu Arg Gly Ala Leu Ala Thr Val Asp Arg Asp Tyr Gly Ile Leu
            290                295                300

Asn Lys Val Phe His Asn Ile Thr Asp Thr His Val Ala His His Leu
305                 310                315                320

Phe Ser Thr Met Pro His Tyr Asn Ala Met Glu Ala Thr Lys Ala Ile
                325                330                335

Lys Pro Ile Leu Gly Asp Tyr Tyr Gln Phe Asp Gly Thr Pro Trp Tyr
            340                345                350

Val Ala Met Tyr Arg Glu Ala Lys Glu Cys Ile Tyr Val Glu Pro Asp
            355                360                365

Arg Glu Gly Asp Lys Lys Gly Val Tyr Trp Tyr Asn Asn Lys Leu
            370                375                380

<210> SEQ ID NO 7
<211> LENGTH: 384
<212> TYPE: PRT
<213> ORGANISM: Brassica napus
<220> FEATURE:
<221> NAME/KEY: misc_feature
<222> LOCATION: (384)..(384)
<223> OTHER INFORMATION: Xaa can be any naturally occurring amino acid
```

<400> SEQUENCE: 7

```
Met Gly Ala Gly Gly Arg Met Gln Val Ser Pro Ser Lys Lys Ser
1               5                   10                  15

Glu Thr Asp Asn Ile Lys Arg Val Pro Cys Glu Thr Pro Pro Phe Thr
            20                  25                  30

Val Gly Glu Leu Lys Lys Ala Ile Pro Pro His Cys Phe Lys Arg Ser
        35                  40                  45

Ile Pro Arg Ser Phe Ser His Leu Ile Trp Asp Ile Ile Ala Ser
    50                  55                  60

Cys Phe Tyr Tyr Val Ala Thr Thr Tyr Phe Pro Leu Leu Pro Asn Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His Ala Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Arg
145                 150                 155                 160

Arg Ser Gln Thr Ser Ser Gly Thr Ala Ser Thr Ser Thr Thr Phe Gly
                165                 170                 175

Arg Thr Val Met Leu Thr Val Gln Phe Thr Leu Gly Trp Pro Leu Tyr
            180                 185                 190

Leu Ala Phe Asn Val Ser Gly Arg Pro Tyr Asp Gly Phe Ala Cys
        195                 200                 205

His Phe His Pro Asn Ala Pro Ile Tyr Asn Asp Arg Glu Arg Leu Gln
    210                 215                 220

Ile Tyr Ile Ser Asp Ala Gly Ile Leu Ala Val Cys Tyr Gly Leu Leu
225                 230                 235                 240

Pro Tyr Ala Ala Val Gln Gly Val Ala Ser Met Val Cys Phe Leu Arg
                245                 250                 255

Val Pro Leu Leu Ile Val Asn Gly Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Gln Gly Phe His Asn Ile Thr Asp Thr His Glu Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Gln Phe Asp Gly Thr Pro Val Val
            340                 345                 350

Lys Ala Met Trp Arg Glu Ala Lys Glu Cys Ile Tyr Val Glu Pro Asp
        355                 360                 365

Arg Gln Gly Glu Lys Lys Gly Val Phe Trp Tyr Asn Asn Lys Leu Xaa
    370                 375                 380
```

<210> SEQ ID NO 8
<211> LENGTH: 309
<212> TYPE: PRT
<213> ORGANISM: Glycine max

-continued

```
<400> SEQUENCE: 8

Ser Leu Leu Thr Ser Phe Ser Tyr Val Val Tyr Asp Leu Ser Phe Ala
1               5                   10                  15

Phe Ile Phe Tyr Ile Ala Thr Thr Tyr Phe His Leu Leu Pro Gln Pro
            20                  25                  30

Phe Ser Leu Ile Ala Trp Pro Ile Tyr Trp Val Leu Gln Gly Cys Leu
        35                  40                  45

Leu Thr Arg Val Cys Gly His His Ala Phe Ser Lys Tyr Gln Trp Val
    50                  55                  60

Asp Asp Val Val Gly Leu Thr Leu His Ser Thr Leu Val Pro Tyr
65                  70                  75                  80

Phe Ser Trp Lys Ile Ser His Arg Arg His His Ser Asn Thr Gly Ser
                85                  90                  95

Leu Asp Arg Asp Glu Arg Val Lys Val Ala Trp Phe Ser Lys Tyr Leu
            100                 105                 110

Asn Asn Pro Leu Gly Arg Ala Val Ser Leu Leu Val Thr Leu Thr Ile
        115                 120                 125

Gly Trp Pro Met Tyr Leu Ala Phe Asn Val Ser Gly Arg Pro Tyr Asp
130                 135                 140

Ser Phe Ala Ser His Tyr His Pro Tyr Arg Val Arg Leu Leu Ile Tyr
145                 150                 155                 160

Val Ser Asp Val Ala Leu Phe Ser Val Thr Tyr Ser Leu Tyr Arg Val
                165                 170                 175

Ala Thr Leu Lys Gly Leu Val Trp Leu Leu Cys Val Tyr Gly Val Pro
            180                 185                 190

Leu Leu Ile Val Asn Gly Phe Leu Val Thr Ile Thr Tyr Leu Arg Val
        195                 200                 205

His Tyr Asp Ser Ser Glu Trp Asp Trp Leu Lys Gly Ala Leu Ala Thr
    210                 215                 220

Met Asp Arg Asp Tyr Gly Ile Leu Asn Lys Val Phe His His Ile Thr
225                 230                 235                 240

Asp Thr His Val Ala His His Leu Phe Ser Thr Met Pro His Tyr His
                245                 250                 255

Leu Arg Val Lys Pro Ile Leu Gly Glu Tyr Tyr Gln Phe Asp Asp Thr
            260                 265                 270

Pro Phe Tyr Lys Ala Leu Trp Arg Glu Ala Arg Glu Cys Leu Tyr Val
        275                 280                 285

Glu Pro Asp Glu Gly Thr Ser Glu Lys Gly Val Tyr Trp Tyr Arg Asn
290                 295                 300

Lys Tyr Leu Arg Val
305

<210> SEQ ID NO 9
<211> LENGTH: 302
<212> TYPE: PRT
<213> ORGANISM: Glycine max

<400> SEQUENCE: 9

Phe Ser Tyr Val Val Tyr Asp Leu Thr Ile Ala Phe Cys Leu Tyr Tyr
1               5                   10                  15

Val Ala Thr His Tyr Phe His Leu Leu Pro Gly Pro Leu Ser Phe Arg
            20                  25                  30

Gly Met Ala Ile Tyr Trp Ala Val Gln Gly Cys Ile Leu Thr Gly Val
        35                  40                  45
```

```
Trp Val Val Ala Phe Ser Asp Tyr Gln Leu Leu Asp Asp Ile Val Gly
 50                  55                  60

Leu Ile Leu His Ser Ala Leu Leu Val Pro Tyr Phe Ser Trp Lys Tyr
 65                  70                  75                  80

Ser His Arg Arg His His Ser Asn Thr Gly Ser Leu Glu Arg Asp Glu
                 85                  90                  95

Val Phe Val Pro Lys Val Ser Lys Tyr Leu Asn Asn Pro Pro Gly Arg
                100                 105                 110

Val Leu Thr Leu Ala Val Thr Leu Thr Leu Gly Trp Pro Leu Tyr Leu
                115                 120                 125

Ala Leu Asn Val Ser Gly Arg Pro Tyr Asp Arg Phe Ala Cys His Tyr
130                 135                 140

Asp Pro Tyr Gly Pro Ile Tyr Ser Val Ile Ser Asp Ala Gly Val Leu
145                 150                 155                 160

Ala Val Val Tyr Gly Leu Phe Arg Leu Ala Met Ala Lys Gly Leu Ala
                165                 170                 175

Trp Val Val Cys Val Tyr Gly Val Pro Leu Leu Val Val Asn Gly Phe
                180                 185                 190

Leu Val Leu Ile Thr Phe Leu Gln His Thr His Val Ser Glu Trp Asp
                195                 200                 205

Trp Leu Arg Gly Ala Leu Ala Thr Val Asp Arg Asp Tyr Gly Ile Leu
210                 215                 220

Asn Lys Val Phe His Asn Ile Thr Asp Thr His Val Ala His His Leu
225                 230                 235                 240

Phe Ser Thr Met Pro His Tyr His Ala Met Glu Ala Thr Val Glu Tyr
                245                 250                 255

Tyr Arg Phe Asp Glu Thr Pro Phe Val Lys Ala Met Trp Arg Glu Ala
                260                 265                 270

Arg Glu Cys Ile Tyr Val Glu Pro Asp Gln Ser Thr Glu Ser Lys Gly
                275                 280                 285

Val Phe Trp Tyr Asn Asn Lys Leu Ala Met Glu Ala Thr Val
                290                 295                 300
```

<210> SEQ ID NO 10
<211> LENGTH: 372
<212> TYPE: PRT
<213> ORGANISM: Zea mays
<220> FEATURE:
<221> NAME/KEY: misc_feature
<222> LOCATION: (372)..(372)
<223> OTHER INFORMATION: Xaa can be any naturally occurring amino acid

<400> SEQUENCE: 10

```
Met Gly Ala Gly Gly Arg Met Thr Glu Lys Glu Arg Glu Lys Gln Glu
 1                   5                  10                  15

Gln Leu Ala Arg Ala Thr Gly Gly Ala Ala Met Gln Arg Ser Pro Val
                 20                  25                  30

Glu Lys Pro Pro Phe Thr Leu Gly Gln Ile Lys Lys Ala Ile Pro Pro
                 35                  40                  45

His Cys Phe Glu Arg Ser Val Leu Lys Ser Phe Ser Tyr Val Val His
                 50                  55                  60

Asp Leu Val Ile Ala Ala Ala Leu Leu Tyr Phe Ala Leu Ala Ile Ile
 65                  70                  75                  80

Pro Ala Leu Pro Ser Pro Leu Arg Tyr Ala Ala Trp Pro Leu Tyr Trp
                 85                  90                  95

Ile Ala Gln Gly Ala Phe Ser Asp Tyr Ser Leu Leu Asp Val Val
                100                 105                 110
```

Gly Leu Val Leu His Ser Ser Leu Met Val Pro Tyr Phe Ser Trp Lys
            115                 120                 125

Tyr Ser His Arg Arg His His Ser Asn Thr Gly Ser Leu Glu Arg Asp
130                 135                 140

Glu Val Phe Val Pro Lys Lys Lys Glu Ala Leu Pro Trp Tyr Thr Pro
145                 150                 155                 160

Tyr Val Tyr Asn Asn Pro Val Gly Arg Val His Ile Val Gln
            165                 170                 175

Leu Thr Leu Gly Trp Pro Leu Tyr Leu Ala Thr Asn Ala Ser Gly Arg
            180                 185                 190

Pro Tyr Pro Arg Phe Ala Cys His Phe Asp Pro Tyr Gly Pro Ile Tyr
            195                 200                 205

Asn Asp Arg Glu Arg Ala Gln Ile Phe Val Ser Asp Ala Gly Val Val
        210                 215                 220

Ala Val Ala Phe Gly Leu Tyr Lys Leu Ala Ala Phe Gly Val Trp
225                 230                 235                 240

Trp Val Val Arg Val Tyr Ala Val Pro Leu Leu Ile Val Asn Ala Trp
                245                 250                 255

Leu Val Leu Ile Thr Tyr Leu Gln His Thr His Pro Ser Leu Pro His
            260                 265                 270

Tyr Asp Ser Ser Glu Trp Asp Trp Leu Arg Gly Ala Leu Ala Thr Met
        275                 280                 285

Asp Arg Asp Tyr Gly Ile Leu Asn Arg Val Phe His Asn Ile Thr Asp
290                 295                 300

Thr His Val Ala His His Leu Phe Ser Thr Met Pro His Tyr His Ala
305                 310                 315                 320

Met Glu Ala Thr Lys Ala Ile Arg Pro Ile Leu Gly Asp Tyr Tyr His
                325                 330                 335

Phe Asp Pro Thr Pro Val Ala Lys Ala Thr Trp Arg Glu Ala Gly Glu
            340                 345                 350

Cys Ile Tyr Val Glu Pro Glu Asp Arg Lys Gly Val Phe Trp Tyr Asn
        355                 360                 365

Lys Lys Phe Xaa
    370

<210> SEQ ID NO 11
<211> LENGTH: 224
<212> TYPE: PRT
<213> ORGANISM: Ricinus communis

<400> SEQUENCE: 11

Trp Val Met Ala His Asp Cys Gly His His Ala Phe Ser Asp Tyr Gln
1               5                   10                  15

Leu Leu Asp Asp Val Val Gly Leu Ile Leu His Ser Cys Leu Leu Val
            20                  25                  30

Pro Tyr Phe Ser Trp Lys His Ser Arg Arg His His Ser Asn Thr
            35                  40                  45

Gly Ser Leu Glu Arg Asp Glu Val Phe Val Pro Lys Lys Lys Ser Ser
        50                  55                  60

Ile Arg Trp Tyr Ser Lys Tyr Leu Asn Asn Pro Gly Arg Ile Met
65                  70                  75                  80

Thr Ile Ala Val Thr Leu Ser Leu Gly Trp Pro Leu Tyr Leu Ala Phe
                85                  90                  95

Asn Val Ser Gly Arg Pro Tyr Asp Arg Phe Ala Cys His Tyr Asp Pro
            100                 105                 110

-continued

```
Tyr Gly Pro Ile Tyr Asn Asp Arg Glu Arg Ile Glu Ile Phe Ile Ser
        115                 120                 125

Asp Ala Gly Val Leu Ala Val Thr Phe Gly Leu Tyr Gln Leu Ala Ile
    130                 135                 140

Ala Lys Gly Leu Ala Trp Val Val Cys Val Tyr Gly Val Pro Leu Leu
145                 150                 155                 160

Val Val Asn Ser Phe Leu Val Leu Ile Thr Phe Leu Gln His Thr His
                165                 170                 175

Pro Ala Leu Pro His Tyr Asp Ser Ser Glu Trp Asp Trp Leu Arg Gly
            180                 185                 190

Ala Leu Ala Thr Val Asp Arg Asp Tyr Gly Ile Leu Asn Lys Val Phe
        195                 200                 205

His Asn Ile Thr Asp Thr Gln Val Ala His His Leu Phe Thr Met Pro
    210                 215                 220

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gctcttttgt gcgctcattc                                               20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
cggtaccaga aaacgccttg                                               20

<210> SEQ ID NO 14
<211> LENGTH: 20
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 14
taywsncaym gnmgncayca                                               20

<210> SEQ ID NO 15
<211> LENGTH: 21
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (7)..(7)
```

```
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 15
rtgrtgngcn acrtgngtrt c                                            21
```

PRODUCTION OF HYDROXYLATED FATTY ACIDS IN GENETICALLY MODIFIED PLANTS

CROSS-REFERENCE TO RELATED APPLICATION

This is a divisional application of U.S. application Ser. No. 11/058,746, filed Feb. 16, 2005, now abandoned, which is a divisional of U.S. application Ser. No. 09/885,189, filed Jun. 21, 2001, now U.S. Pat. No. 6,936,728, which is a continuation application of U.S. application Ser. No. 08/597,313, filed Feb. 6, 1996, now U.S. Pat. No. 6,310,194, which is a continuation-in-part application of U.S. application Ser. No. 08/530,862, filed Sep. 20, 1995, now U.S. Pat. No. 6,291,742, which is a continuation-in-part application of U.S. application Ser. No. 08/320,982, filed Oct. 11, 1994, now U.S. Pat. No. 5,801,026, which is a continuation-in-part application of U.S. patent application Ser. No. 08/314,596, filed Sep. 26, 1994, now U.S. Pat. No. 5,668,292, all of which are herein incorporated by reference in their entirety.

GOVERNMENT RIGHTS

The invention described herein was made in the course of work under grant number DE-FG02-94ER20133 from the U.S. Department of Energy and grant No. MCB9305269 from the National Science Foundation. Therefore, the U.S. Government has certain rights under this invention.

TECHNICAL FIELD

The present invention concerns the identification of nucleic acid sequences and constructs, and methods related thereto, and the use of these sequences and constructs to produce genetically modified plants for the purpose of altering the fatty acid composition of plant oils, waxes and related compounds.

DEFINITIONS

The subject of this invention is a class of enzymes that introduce a hydroxyl group into several different fatty acids resulting in the production of several different kinds of hydroxylated fatty acids. In particular, these enzymes catalyze hydroxylation of oleic acid to 12-hydroxy oleic acid and icosenoic acid to 14-hydroxy icosenoic acid. Other fatty acids such as palmitoleic and erucic acids may also be substrates. Since it is not possible to refer to the enzyme by reference to a unique substrate or product, we refer to the enzyme throughout as kappa hydroxylase to indicate that the enzyme introduces the hydroxyl three carbons distal (i.e., away from the carboxyl carbon of the acyl chain) from a double bond located near the center of the acyl chain.

The following fatty acids are also the subject of this invention: ricinoleic acid, 12-hydroxyoctadec-cis-9-enoic acid (12OH-18:$1^{cis\Delta 9}$); lesquerolic acid, 14-hydroxy-cis-11-icosenoic acid (14OH-20:$1^{cis\Delta 11}$); densipolic acid, 12-hydroxyoctadec-cis-9,15-dienoic acid (12OH-18:$2^{cis\Delta 9,15}$); auricolic acid, 14-hydroxy-cis-11,17-icosadienoic acid (14OH-20:$2^{cis\Delta 11,17}$); hydroxyerucic, 16-hydroxydocos-cis-13-enoic acid (16OH22:$1^{cis\Delta 13}$); hydroxypalmitoleic, 12-hydroxyhexadec-cis-9-enoic (12OH-16:$1^{cis\Delta 9}$); icosenoic acid (20:$1^{cis\Delta 11}$). It will be noted that icosenoic acid is spelled eicosenoic acid in some countries.

BACKGROUND

Extensive surveys of the fatty acid composition of seed oils from different species of higher plants have resulted in the identification of at least 33 structurally distinct monohydroxylated plant fatty acids, and 12 different polyhydroxylated fatty acids that are accumulated by one or more plant species (reviewed by van de Loo et al. 1993). Ricinoleic acid, the principal constituent of the seed oil from the castor plant *Ricinus communis* (L.), is of commercial importance. We have previously described the cloning of a gene from this species that encodes a fatty acid hydroxylase, and the use of this gene to produce ricinoleic acid in transgenic plants of other species (see U.S. patent application Ser. No. 08/320,982, filed Oct. 11, 1994). The scientific evidence supporting the claims in that patent application were subsequently published (van de Loo et al., 1995).

The use of the castor hydroxylase gene to also produce other hydroxylated fatty acids such as lesquerolic acid, densipolic acid, hydroxypalmitoleic, hydroxyerucic and auricolic acid in transgenic plants is the subject of this invention. In addition, the identification of a gene encoding a homologous hydroxylase from *Lesquerella fendleri*, and the use of this gene to produce these hydroxylated fatty acids in transgenic plants is the subject of this invention.

Castor is a minor oilseed crop. Approximately 50% of the seed weight is oil (triacylglycerol) in which 85-90% of total fatty acids are the hydroxylated fatty acid, ricinoleic acid. Oil pressed or extracted from castor seeds has many industrial uses based upon the properties endowed by the hydroxylated fatty acid. The most important uses are production of paints and varnishes, nylon-type synthetic polymers, resins, lubricants, and cosmetics (Atsmon 1989).

In addition to oil, the castor seed contains the extremely toxic protein ricin, allergenic proteins, and the alkaloid ricinine. These constituents preclude the use of the untreated seed meal (following oil extraction) as a livestock feed, normally an important economic aspect of oilseed utilization. Furthermore, with the variable nature of castor plants and a lack of investment in breeding, castor has few favorable agronomic characteristics.

For a combination of these reasons, castor is no longer grown in the United States and the development of an alternative domestic source of hydroxylated fatty acids would be attractive. The production of ricinoleic acid, the important constituent of castor oil, in an established oilseed crop through genetic engineering would be a particularly effective means of creating a domestic source.

Because there is no practical source of lesquerolic, densipolic and auricolic acids from plants that are adapted to modern agricultural practices, there is currently no large-scale use of these fatty acids by industry. However, the fatty acids would have uses similar to those of ricinoleic acid if they could be produced in large quantities at comparable cost to other plant-derived fatty acids (Smith 1985).

Plant species, such as certain species in the genus *Lesquerella*, that accumulate a high proportion of these fatty acids, have not been domesticated and are not currently considered a practical source of fatty acids (Hirsinger, 1989). This invention represents a useful step toward the eventual production of these and other hydroxylated fatty acids in transgenic plants of agricultural importance.

The taxonomic relationships between plants having similar or identical kinds of unusual fatty acids have been examined (van de Loo et al., 1993). In some cases, particular fatty acids occur mostly or solely in related taxa. In other cases there does not appear to be a direct link between taxonomic relationships and the occurrence of unusual fatty acids. In this respect, ricinoleic acid has now been identified in 12 genera from 10 families (reviewed in van de Loo et al., 1993). Thus, it appears that the ability to synthesize hydroxylated fatty acids has evolved several times independently during the radiation of the angiosperms. This suggested to us that the enzymes which introduce hydroxyl groups into fatty acids arose by minor modifications of a related enzyme.

Indeed, as shown herein, the sequence similarity between Δ12 fatty acid desaturases and the kappa hydroxylase from castor is so high that it is not possible to unambiguously determine whether a particular enzyme is a desaturase or a hydroxylase on the basis of evidence in the scientific literature. Similarly, a patent application (PCT/US93/09987) that purports to teach the isolation and use of Δ12 fatty acid desaturases does not teach how to distinguish a hydroxylase from a desaturase. In view of the importance of being able to distinguish between these activities for the purpose of genetic engineering of plant oils, the utility of that application is limited to the several instances where direct experimental evidence (e.g., altered fatty acid composition in transgenic plants) was presented to support the assignment of function. A method for distinguishing between fatty acid desaturases and fatty acid hydroxylases on the basis of amino acid sequence of the enzyme is also a subject of this invention.

A feature of hydroxylated or other unusual fatty acids is that they are generally confined to seed triacylglycerols, being largely excluded from the polar lipids by unknown mechanisms (Battey and Ohlrogge 1989; Prasad et al., 1987). This is particularly intriguing since diacylglycerol is a precursor of both triacylglycerol and polar lipid. With castor microsomes, there is some evidence that the pool of ricinoleoyl-containing polar lipid is minimized by a preference of diacylglycerol acyltransferase for ricinoleate-containing diacylglycerols (Bafor et al. 1991). Analyses of vegetative tissues have generated few reports of unusual fatty acids, other than those occurring in the cuticle. The cuticle contains various hydroxylated fatty acids which are interesterified to produce a high molecular weight polyester which serves a structural role. A small number of other exceptions exist in which unusual fatty acids are found in tissues other than the seed.

The biosynthesis of ricinoleic acid from oleic acid in the developing endosperm of castor (*Ricinus communis*) has been studied by a variety of methods. Morris (1967) established in double-labeling studies that hydroxylation occurs directly by hydroxyl substitution rather than via an unsaturated-, keto- or epoxy-intermediate. Hydroxylation using oleoyl-CoA as precursor can be demonstrated in crude preparations or microsomes, but activity in microsomes is unstable and variable, and isolation of the microsomes involved a considerable, or sometimes complete loss of activity (Galliard and Stumpf, 1966; Moreau and Stumpf, 1981). Oleic acid can replace oleoyl-CoA as a precursor, but only in the presence of CoA, $Mg^{2+}$ and ATP (Galliard and Stumpf, 1966) indicating that activation to the acyl-CoA is necessary. However, no radioactivity could be detected in ricinoleoyl-CoA (Moreau and Stumpf, 1981). These and more recent observations (Bafor et al., 1991) have been interpreted as evidence that the substrate for the castor oleate hydroxylase is oleic acid esterified to phosphatidyicholine or another phospholipid.

The hydroxylase is sensitive to cyanide and azide, and dialysis against metal chelators reduces activity, which could be restored by addition of $FeSO_4$, suggesting iron involvement in enzyme activity (Galliard and Stumpf, 1966). Ricinoleic acid synthesis requires molecular oxygen (Galliard and Stumpf, 1966; Moreau and Stumpf 1981) and requires NAD(P)H to reduce cytochrome b5 which is thought to be the intermediate electron donor for the hydroxylase reaction (Smith et al., 1992). Carbon monoxide does not inhibit hydroxylation, indicating that a cytochrome P450 is not involved (Galliard and Stumpf, 1966; Moreau and Stumpf 1981). Data from a study of the substrate specificity of the hydroxylase show that all substrate parameters (i.e., chain length and double bond position with respect to both ends) are important; deviations in these parameters caused reduced activity relative to oleic acid (Howling et al., 1972). The position at which the hydroxyl was introduced, however, was determined by the position of the double bond, always being three carbons distal. Thus, the castor acyl hydroxylase enzyme can produce a family of different hydroxylated fatty acids depending on the availability of substrates. Thus, as a matter of convenience, we refer to the enzyme throughout as a kappa hydroxylase (rather than an oleate hydroxylase) to indicate the broad substrate specificity.

The castor kappa hydroxylase has many superficial similarities to the microsomal fatty acyl desaturases (Browse and Somerville, 1991). In particular, plants have a microsomal oleate desaturase active at the Δ12 position. The substrate of this enzyme (Schmidt et al., 1993) and of the hydroxylase (Bafor et al., 1991) appears to be a fatty acid esterified to the sn-2 position of phosphatidylcholine. When oleate is the substrate, the modification occurs at the same position (Δ12) in the carbon chain, and requires the same cofactors, namely electrons from NADH via cytochrome $b_5$ and molecular oxygen. Neither enzyme is inhibited by carbon monoxide (Moreau and Stumpf, 1981), the characteristic inhibitor of cytochrome P450 enzymes.

There do not appear to have been any published biochemical studies of the properties of the hydroxylase enzyme(s) in *Lesquerella*.

Conceptual Basis of the Invention

In U.S. patent application Ser. No. 08/320,982, we described the use of a cDNA clone from castor for the production of ricinoleic acid in transgenic plants. As noted above, biochemical studies by others had suggested that the castor hydroxylase may not have strict specificity for oleic acid but would also catalyze hydroxylation of other fatty acids such as icosenoic acid ($20:1^{cis\Delta 11}$) (Howling et al., 1972). Based on these studies, our previous application Ser. No. 08/320,982 noted in Example 2 that the expression of the castor hydroxylase in transgenic plants of species such as *Brassica napus* and *Arabidopsis thaliana* that accumulate fatty acids such as icosenoic acid ($20:1^{cis\Delta 11}$) and erucic acid (13-docosenoic acid; $22:1^{cis\Delta 13}$) would be expected to accumulate some of the hydroxylated derivatives of these fatty acids due to the activity of the hydroxylase on these fatty acids. We have now obtained additional direct evidence for such a claim based on the production of ricinoleic, lesquerolic, densipolic and auricolic fatty acids in transgenic *Arabidopsis* plants and have included such evidence herein as Example 1.

In Example 3 of the previous application, we taught the various methods by which the castor hydroxylase clone and sequences derived thereof could be used to identify other hydroxylase clones from plant species such as *Lesquerella fendleri* that are known to accumulate hydroxylated fatty acids in seed oils. In this continuation we have provided an example of the use of that aspect of the invention for the isolation of a novel hydroxylase gene from *Lesquerella fendleri*.

In view of the high degree of sequence similarity between Δ12 fatty acid desaturases and the castor hydroxylase (van de Loo et al., 1995), the validity of claims (e.g., PCT WO 94/11516) for the use of desaturase or hydroxylase genes or sequences derived therefrom for the identification of genes of identical function from other species must be viewed with skepticism. In this application, we teach a method by which hydroxylase genes can be distinguished from desaturases and describe methods by which Δ12 desaturases can be converted to hydroxylases by the modification of the gene encoding the desaturases. A mechanistic basis for the similar reaction mechanisms of desaturases and hydroxylases was presented in the earlier patent application Ser. No. 08/320,982. Briefly, the available evidence suggests that fatty acid desaturases have a similar reaction mechanism to the bacterial enzyme methane monooxygenase which catalyses a reaction involving oxygen-atom transfer ($CH_4 \rightarrow CH_3OH$) (van de Loo et al., 1993). The cofactor in the hydroxylase component of methane monooxygenase is termed a μ-oxo bridged diiron cluster (FeOFe). The two iron atoms of the FeOFe cluster are liganded by protein-derived nitrogen or oxygen atoms, and are tightly redox-coupled by the covalently-bridging oxygen atom. The FeOFe cluster accepts two electrons, reducing it to the diferrous state, before oxygen binding. Upon oxygen binding, it is likely that heterolytic cleavage also occurs, leading to a high valent oxoiron reactive species that is stabilized by resonance rearrangements possible within the tightly coupled FeOFe cluster. The stabilized high-valent oxoiron state of methane monooxygenase is capable of proton extraction from methane, followed by oxygen transfer, giving methanol. The FeOFe cofactor has been shown to be directly relevant to plant fatty acid modifications by the demonstration that castor stearoyl-ACP desaturase contains this type of cofactor (Fox et al., 1993).

On the basis of the foregoing considerations, we hypothesized that the castor oleate hydroxylase is a structurally modified fatty acyl desaturase, based upon three arguments. The first argument involves the taxonomic distribution of plants containing ricinoleic acid. Ricinoleic acid has been found in 12 genera of 10 families of higher plants (reviewed in van de Loo et al., 1993). Thus, plants in which ricinoleic acid occurs are found throughout the plant kingdom, yet close relatives of these plants do not contain the unusual fatty acid. This pattern suggests that the ability to synthesize ricinoleic acid has arisen (and been lost) several times independently, and is therefore a quite recent divergence. In other words, the ability to synthesize ricinoleic acid has evolved rapidly, suggesting that a relatively minor genetic change in the structure of the ancestral enzyme was necessary to accomplish it.

The second argument is that many biochemical properties of castor kappa hydroxylase are similar to those of the microsomal desaturases, as discussed above (e.g., both preferentially act on fatty acids esterified to the sn-2 position of phosphatidylcholine, both use cytochrome b5 as an intermediate electron donor, both are inhibited by cyanide, both require molecular oxygen as a substrate, both are thought to be located in the endoplasmic reticulum).

The third argument stems from the discussion of oxygenase cofactors above, in which it is suggested that the plant membrane bound fatty acid desaturases may have a μ-oxo bridged diiron cluster-type cofactor, and that such cofactors are capable of catalyzing both fatty acid desaturations and hydroxylations, depending upon the electronic and structural properties of the protein active site.

Taking these three arguments together, it was hypothesized that kappa hydroxylase of castor endosperm is homologous to the microsomal oleate Δ12 desaturase found in all plants. The evidence supporting this hypothesis was disclosed in the previous patent application Ser. No. 08/320,982. A number of genes encoding microsomal Δ12 desaturases from various species have recently been cloned (Okuley et al., 1994) and substantial information about the structure of these enzymes is now known (Shanklin et al. 1994). Hence, in the following invention we teach how to use structural information about fatty acyl desaturases to isolate kappa hydroxylase genes of this invention. This example teaches the method by which any carbon-monoxide insensitive plant fatty acyl hydroxylase gene can be identified by one skilled in the art.

An unpredicted outcome of our studies on the castor hydroxylase gene in transgenic *Arabidopsis* plants was the discovery that expression of the hydroxylase leads to increased accumulation of oleic acid in seed lipids. Because of the low nucleotide sequence homology between the castor hydroxylase and the Δ12-desaturase (about 67%), we consider it unlikely that this effect is due to silencing (also called sense-suppression or cosuppression) of the expression of the desaturase gene by the hydroxylase gene. Whatever the basis for the effect, this invention teaches the use of hydroxylase genes to alter the level of fatty acid unsaturation in transgenic plants. On the basis of a hypothesis about the mechanisms of the effect, this invention also teaches the use of genetically modified hydroxylase and desaturase genes to achieve directed modification of fatty acid unsaturation levels.

BRIEF DESCRIPTION OF THE DRAWINGS

FIG. 1B, O-TMS-methyl densipoleate; FIG. 1C, O-TMS-methyl-lesqueroleate; and FIG. 1D, O-TMS-methyllauricoleate).

FIG. 2 shows the fragmentation pattern of trimethylsilylated methyl esters of hydroxy fatty acids.

FIGS. 4A-D show the mass spectra of novel fatty acids found in seeds of transgenic plants. FIG. 4A shows the mass spectrum of peak 10 from FIG. 3B. FIG. 4B shows the mass spectrum of peak 11 from FIG. 3B. FIG. 4C shows the mass spectrum of peak 12 from FIG. 3B. FIG. 4D shows the mass spectrum of peak 13 from FIG. 3B.

FIG. 5 shows the nucleotide sequence of pLesq2 (SEQ ID NO:1).

FIG. 6 shows the nucleotide sequence of pLesq3 (SEQ ID NO:2).

FIGS. 8A-B show the nucleotide sequence of genomic clone encoding pLesq-HYD (SEQ ID NO:3), and the deduced amino acid sequence of hydroxylase enzyme encoded by the gene (SEQ ID NO:4).

FIGS. 9A-B show multiple sequence alignment of deduced amino acid sequences for kappa hydroxylases and microsomal Δ12 desaturases. Abbreviations are: Rcfah12, fah12 hydroxylase gene from *R. communis* (van de Loo et al., 1995); Lffah12, kappa hydroxylase gene from *L. fendleri*; Atfad2, fad2 desaturase from *Arabidopsis thaliana* (Okuley et al., 1994); Gmfad2-1, fad2 desaturase from *Glycine max* (GenBank accession number L43920); Gmfad2-2, fad2 desaturase from *Glycine max* (Genbank accession number L43921); Zmfad2, fad2 desaturase from *Zea mays* (PCT/US93/09987); Rcfad2, fragment of fad2 desaturase from *R. communis* (PCT/US93/09987); Bnfad2, fad2 desaturase from *Brassica napus* (PCT/US93/09987); LFFAH12.AMI, SEQ ID NO:4; FAH12.AMI, SEQ ID NO:5; ATFAD2.AMI, SEQ ID NO:6;

BNFAD2.AMI, SEQ ID NO:7; GMFAD2-1.AMI, SEQ ID NO:8; GMFAD2-2.AMI, SEQ ID NO:9; ZMFAD2.AMI, SEQ ID NO:10; and RCFAD2.AMI, SEQ ID NO:11.

Figure 10:
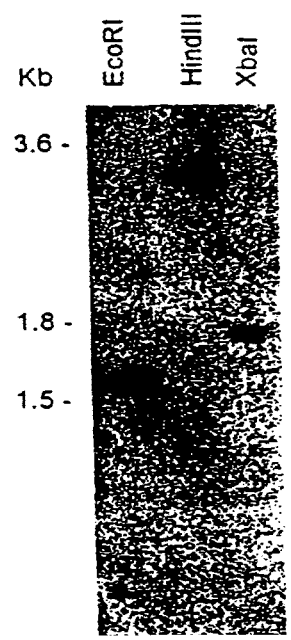

FIG. 10 shows a Southern blot of genomic DNA from *L. fendleri* probed with pLesq-HYD. E=EcoRI, H=HindIII, X=XbaI.

Figure 11:
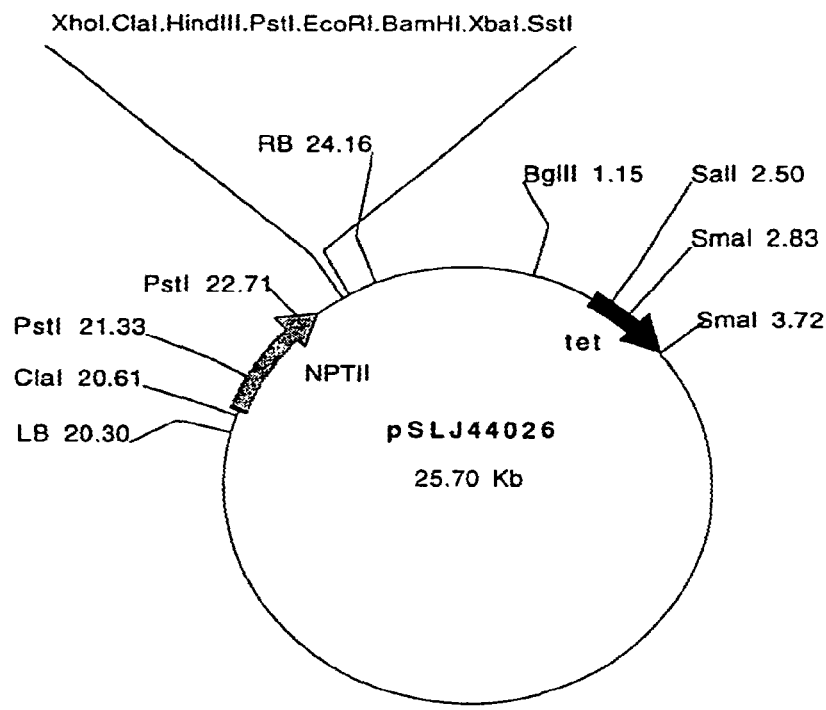

FIG. 11 shows a map of binary Ti plasmid pSLJ44024.

Figure 12:
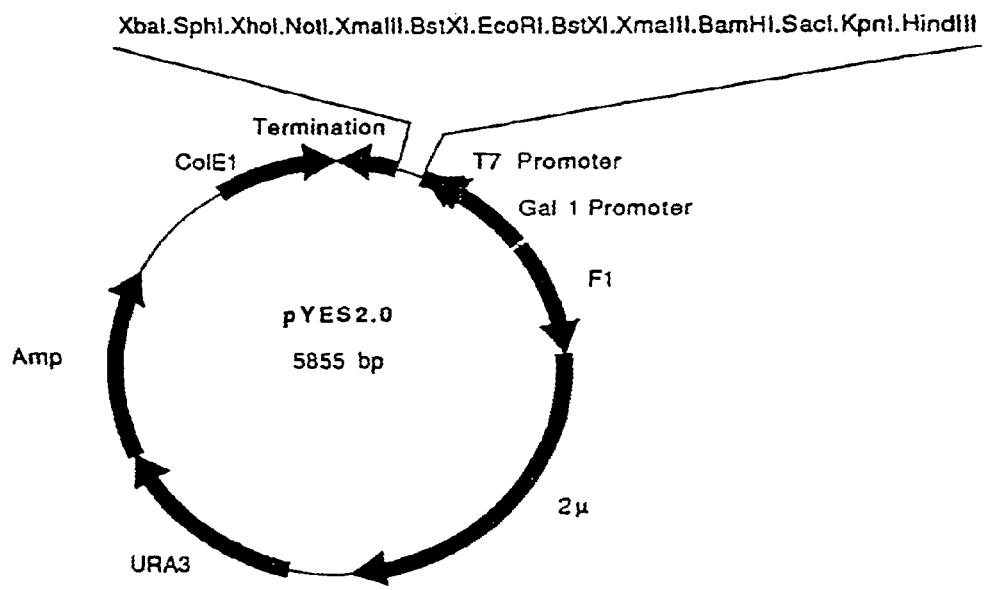

FIG. 12 shows a map of plasmid pYES2.0

Figure 13:
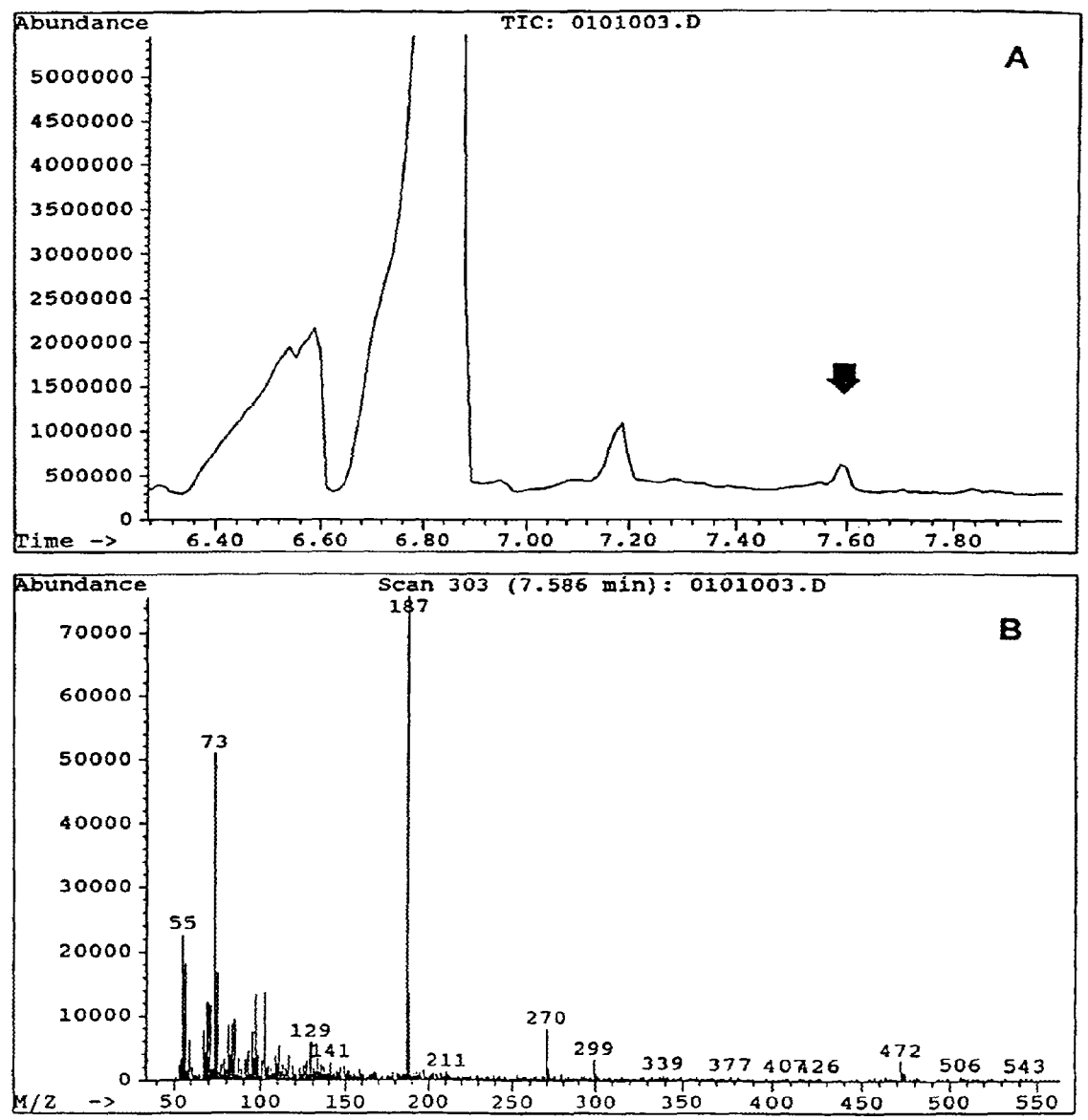

FIG. 13 shows part of a gas chromatogram of derivatized fatty acids from yeast cells that contain plasmid pLesqYes in which expression of the hydroxylase gene was induced by addition of galactose to the growth medium. The arrow points to a peak that is not present in uninduced cells. The lower part of the figure is the mass spectrum of the peak indicated by the arrow.

SUMMARY OF THE INVENTION

This invention relates to plant fatty acyl hydroxylases. Methods to use conserved amino acid or nucleotide sequences to obtain plant fatty acyl hydroxylases are described. Also described is the use of cDNA clones encoding a plant hydroxylase to produce a family of hydroxylated fatty acids in transgenic plants.

In a first embodiment, this invention is directed to recombinant DNA constructs which can provide for the transcription or transcription and translation (expression) of the plant kappa hydroxylase sequence. In particular, constructs which are capable of transcription or transcription and translation in plant host cells are preferred. Such constructs may contain a variety of regulatory regions including transcriptional initiation regions obtained from genes preferentially expressed in plant seed tissue. In a second aspect, this invention relates to the presence of such constructs in host cells, especially plant host cells which have an expressed plant kappa hydroxylase therein.

In yet another aspect, this invention relates to a method for producing a plant kappa hydroxylase in a host cell or progeny thereof via the expression of a construct in the cell. Cells containing a plant kappa hydroxylase as a result of the production of the plant kappa hydroxylase encoding sequence are also contemplated herein.

In another embodiment, this invention relates to methods of using a DNA sequence encoding a plant kappa hydroxylase for the modification of the proportion of hydroxylated fatty acids produced within a cell, especially plant cells. Plant cells having such a modified hydroxylated fatty acid composition are also contemplated herein.

In a further aspect of this invention, plant kappa hydroxylase proteins and sequences which are related thereto, including amino acid and nucleic acid sequences, are contemplated. Plant kappa hydroxylase exemplified herein includes a *Lesquerella fendleri* fatty acid hydroxylase. This exemplified fatty acid hydroxylase may be used to obtain other plant fatty acid hydroxylases of this invention.

In a further aspect of this invention, a nucleic acid sequence which directs the seed specific expression of an associated polypeptide coding sequence is described. The use of this nucleic acid sequence or fragments derived thereof, to obtain seed-specific expression in higher plants of any coding sequence is contemplated herein.

In a further aspect of this invention, the use of genes encoding fatty acyl hydroxylases of this invention are used to alter the amount of fatty acid unsaturation of seed lipids. We further envision the use of genetically modified hydroxylase and desaturase genes to achieve directed modification of fatty acid unsaturation levels.

DETAILED DESCRIPTION OF THE INVENTION

A genetically transformed plant of the present invention which accumulates hydroxylated fatty acids can be obtained by expressing the double-stranded DNA molecules described in this application.

A plant fatty acid hydroxylase of this invention includes any sequence of amino acids, such as a protein, polypeptide or peptide fragment, or nucleic acid sequences encoding such polypeptides, obtainable from a plant source which demonstrates the ability to catalyze the production of ricinoleic, lesquerolic, hydroxyerucic (16-hydroxydocos-cis-13-enoic acid) or hydroxypalmitoleic (12-hydroxyhexadec-cis-9-enoic) from CoA, ACP or lipid-linked monoenoic fatty acid substrates under plant enzyme reactive conditions. By "enzyme reactive conditions" is meant that any necessary conditions are available in an environment (i.e., such factors as temperature, pH, lack of inhibiting substances) which will permit the enzyme to function.

Preferential activity of a plant fatty acid hydroxylase toward a particular fatty acyl substrate is determined upon comparison of hydroxylated fatty acid product amounts obtained per different fatty acyl substrates. For example, by "oleate preferring" is meant that the hydroxylase activity of the enzyme preparation demonstrates a preference for oleate-containing substrates over other substrates. Although the precise substrate of the castor fatty acid hydroxylase is not known, it is thought to be a monounsaturated fatty acid moiety which is esterified to a phospholipid such as phosphatidylcholine. However, it is also possible that monounsaturated fatty acids esterified to phosphatidylethanolamine, phosphatidic acid or a neutral lipid such as diacylglycerol or a Coenzyme-A thioester may also be substrates.

As noted above, significant activity has been observed in radioactive labelling studies using fatty acyl substrates other than oleate (Howling et al., 1972) indicating that the substrate specificity is for a family of related fatty acyl compounds. Because the castor hydroxylase introduces hydroxy groups three carbons from a double bond, proximal to the methyl carbon of the fatty acid, we term the enzyme a kappa hydroxylase for convenience. Of particular interest, we envision that the castor kappa hydroxylase may be used for production of 12-hydroxy-9-octadecenoic acid (ricinoleate), 12-hydroxy-9-hexadecenoic acid, 14-hydroxy-11-eicosenoic acid, 16-hydroxy-13-docosanoic acid, 9-hydroxy-6-octadecenoic acid by expression in plants species which produce the non-hydroxylated precursors. We also envision production of additionally modified fatty acids such as 12-hydroxy-9,15-octadecadienoic acid that result from desaturation of hydroxylated fatty acids (e.g., 12-hydroxy-9-octadecenoic acid in this example).

We also envision that future advances in the genetic engineering of plants will lead to production of substrate fatty acids, such as icosenoic acid esters, and palmitoleic acid esters in plants that do not normally accumulate such fatty acids. We envision that the invention described herein may be used in conjunction with such future improvements to produce hydroxylated fatty acids of this invention in any plant species that is amenable to directed genetic modification. Thus, the applicability of this invention is not limited in our conception only to those species that currently accumulate suitable substrates.

As noted above, a plant kappa hydroxylase of this invention will display activity towards various fatty acyl substrates. During biosynthesis of lipids in a plant cell, fatty acids are typically covalently bound to acyl carrier protein (ACP), coenzyme A (CoA) or various cellular lipids. Plant kappa hydroxylases which display preferential activity toward lipid-linked acyl substrate are especially preferred because they are likely to be closely associated with normal pathway of storage lipid synthesis in immature embryos. However, activity toward acyl-CoA substrates or other synthetic substrates, for example, is also contemplated herein.

Other plant kappa hydroxylases are obtainable from the specific exemplified sequences provided herein. Furthermore, it will be apparent that one can obtain natural and synthetic plant kappa hydroxylases including modified amino acid sequences and starting materials for synthetic-protein modeling from the exemplified plant kappa hydroxylase and from plant kappa hydroxylases which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

Thus, one skilled in the art will readily recognize that antibody preparations, nucleic acid probes (DNA and RNA) and the like may be prepared and used to screen and recover "homologous" or "related" kappa hydroxylases from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available.

Homologous sequences are found when there is an identity of sequence and may be determined upon comparison of sequence information, nucleic acid or amino acid, or through hybridization reactions between a known kappa hydroxylase and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50-60% sequence identity, and more preferably at least about 70% sequence identity, between the target sequence and the given plant kappa hydroxylase of interest excluding any deletions which may be present, and still be considered related. Amino acid sequences are considered homologous by as little as 25% sequence identity between the two complete mature proteins. (See generally, Doolittle, R. F., OF URFS and ORFS, University Science Books, Calif., 1986.)

A genomic or other appropriate library prepared from the candidate plant source of interest may be probed with conserved sequences from the plant kappa hydroxylase to identify homologously related sequences. Use of an entire cDNA or other sequence may be employed if shorter probe sequences are not identified. Positive clones are then analyzed by restriction enzyme digestion and/or sequencing. When a genomic library is used, one or more sequences may be identified providing both the coding region, as well as the transcriptional regulatory elements of the kappa hydroxylase gene from such plant source. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified (See Gould, et al., 1989 for examples of the use of PCR to isolate homologous genes from taxonomically diverse species).

When longer nucleic acid fragments are employed (>100 bp) as probes, especially when using complete or large cDNA sequences, one would screen with low stringencies (for example, 40-50° C. below the melting temperature of the probe) in order to obtain signal from the target sample with 20-50% deviation, i.e., homologous sequences. (Beltz, et al. 1983).

In a preferred embodiment, a plant kappa hydroxylase of this invention will have at least 60% overall amino acid sequence similarity with the exemplified plant kappa hydroxylase. In particular, kappa hydroxylases which are obtainable from an amino acid or nucleic acid sequence of a castor or *lesquerella* kappa hydroxylase are especially preferred. The plant kappa hydroxylases may have preferential activity toward longer or shorter chain fatty acyl substrates. Plant fatty acyl hydroxylases having oleate-12-hydroxylase activity and eicosenoate-14-hydroxylase activity are both considered homologously related proteins because of in vitro evidence (Howling et al., 1972), and evidence disclosed herein, that the castor kappa hydroxylase will act on both substrates. Hydroxylated fatty acids may be subject to further enzymatic modification by other enzymes which are normally present or are introduced by genetic engineering methods. For example, 14-hydroxy-11,17-eicosadienoic acid, which is present in some *Lesquerella* species (Smith 1985), is thought to be produced by desaturation of 14-hydroxy-11-eicosenoic acid.

Again, not only can gene clones and materials derived thereof be used to identify homologous plant fatty acyl hydroxylases, but the resulting sequences obtained therefrom may also provide a further method to obtain plant fatty acyl hydroxylases from other plant sources. In particular, PCR may be a useful technique to obtain related plant fatty acyl hydroxylases from sequence data provided herein. One skilled in the art will be able to design oligonucleotide probes based upon sequence comparisons or regions of typically highly conserved sequence. Of special interest are polymerase chain reaction primers based on the conserved regions of amino acid sequence between the castor kappa hydroxylase and the *L. fendleri* hydroxylase (SEQ ID NO:4). Details relating to the design and methods for a PCR reaction using these probes are described more fully in the examples.

It should also be noted that the fatty acyl hydroxylases of a variety of sources can be used to investigate fatty acid hydroxylation events in a wide variety of plant and in vivo applications. Because all plants synthesize fatty acids via a common metabolic pathway, the study and/or application of one plant fatty acid hydroxylase to a heterologous plant host may be readily achieved in a variety of species.

Once the nucleic acid sequence is obtained, the transcription, or transcription and translation (expression), of the plant fatty acyl hydroxylases in a host cell is desired to produce a ready source of the enzyme and/or modify the composition of fatty acids found therein in the form of free fatty acids, esters (particularly esterified to glycerolipids or as components of wax esters), estolides, or ethers. Other useful applications may be found when the host cell is a plant host cell, in vitro and in vivo. For example, by increasing the amount of an kappa hydroxylase available to the plant, an increased percentage of ricinoleate or lesqueroleate (14-hydroxy-11-eicosenoic acid) may be provided.

Kappa Hydroxylase

By this invention, a mechanism for the biosynthesis of ricinoleic acid in plants is demonstrated. Namely, that a specific plant kappa hydroxylase having preferential activity toward fatty acyl substrates is involved in the accumulation of hydroxylated fatty acids in at least some plant species. The use of the terms ricinoleate or ricinoleic acid (or lesqueroleate or lesquerolic acid, densipoleate etc.) is intended to include the free acids, the ACP and CoA esters, the salts of these acids, the glycerolipid esters (particularly the triacylglycerol esters), the wax esters, the estolides and the ether derivatives of these acids.

The determination that plant fatty acyl hydroxylases are active in the in vivo production of hydroxylated fatty acids suggests several possibilities for plant enzyme sources. In fact, hydroxylated fatty acids are found in some natural plant species in abundance. For example, three hydroxy fatty acids related to ricinoleate occur in major amounts in seed oils from various *Lesquerella* species. Of particular interest, lesquerolic acid is a 20 carbon homolog of ricinoleate with two additional carbons at the carboxyl end of the chain (Smith 1985). Other natural plant sources of hydroxylated fatty acids include but are not limited to seeds of the *Linum* genus, seeds of *Wrightia* species, *Lycopodium* species, *Strophanthus* species, *Convolvulaces* species, *Calendula* species and many others (van de Loo et al., 1993).

Plants having significant presence of ricinoleate or lesqueroleate or desaturated other or modified derivatives of these fatty acids are preferred candidates to obtain naturally-derived kappa hydroxylases. For example, *Lesquerella densipila* contains a diunsaturated 18 carbon fatty acid with a hydroxyl group (van de Loo et al., 1993) that is thought to be produced by an enzyme that is closely related to the castor kappa hydroxylase, according to the theory on which this invention is based. In addition, a comparison between kappa hydroxylases and between plant fatty acyl hydroxylases which introduce hydroxyl groups at positions other than the 12-carbon of oleate or the 14-carbon of lesqueroleate or on substrates other than oleic acid and icosenoic acid may yield insights for protein modeling or other modifications to create synthetic hydroxylases as discussed above. For example, on the basis of information gained from structural comparisons of the $\Delta12$ desaturases and the kappa hydroxylase, we envision making genetic modifications in the structural genes for $\Delta12$ desaturases that convert these desaturases to kappa-hydroxylases. We also envision making changes in $\Delta15$ hydroxylases that convert these to hydroxylases with comparable substrate specificity to the desaturases (e.g., conversion of $18:2^{\Delta9,12}$ to $15OH-18:2^{\Delta9,12}$. Since the difference between a hydroxylase and a desaturases concerns the disposition of one proton, we envision that by systematically changing the charged groups in the region of the enzyme near the active site, we can effect this change.

Especially of interest are fatty acyl hydroxylases which demonstrate activity toward fatty acyl substrates other than oleate, or which introduce the hydroxyl group at a location other than the C12 carbon. As described above, other plant sources may also provide sources for these enzymes through the use of protein purification, nucleic acid probes, antibody preparations, protein modeling, or sequence comparisons, for example, and of special interest are the respective amino acid and nucleic acid sequences corresponding to such plant fatty acyl hydroxylases. Also as previously described, once a nucleic acid sequence is obtained for the given plant hydroxylase, further plant sequences may be compared and/or probed to obtain homologously related DNA sequences thereto and so on.

Genetic Engineering Applications

As is well known in the art, once a cDNA clone encoding a plant kappa hydroxylase is obtained, it may be used to obtain its corresponding genomic nucleic acid sequences thereto.

The nucleic acid sequences which encode plant kappa hydroxylases may be used in various constructs, for example, as probes to obtain further sequences from the same or other species. Alternatively, these sequences may be used in conjunction with appropriate regulatory sequences to increase levels of the respective hydroxylase of interest in a host cell for the production of hydroxylated fatty acids or study of the enzyme in vitro or in vivo or to decrease or increase levels of the respective hydroxylase of interest for some applications when the host cell is a plant entity, including plant cells, plant parts (including but not limited to seeds, cuttings or tissues) and plants.

A nucleic acid sequence encoding a plant kappa hydroxylase of this invention may include genomic, cDNA or mRNA sequence. By "encoding" is meant that the sequence corresponds to a particular amino acid sequence either in a sense or anti-sense orientation. By "recombinant" is meant that the sequence contains a genetically engineered modification through manipulation via mutagenesis, restriction enzymes, and the like. A cDNA sequence may or may not encode pre-processing sequences, such as transit or signal peptide sequences. Transit or signal peptide sequences facilitate the delivery of the protein to a given organelle and are frequently cleaved from the polypeptide upon entry into the organelle, releasing the "mature" sequence. The use of the precursor DNA sequence is preferred in plant cell expression cassettes.

Furthermore, as discussed above the complete genomic sequence of the plant kappa hydroxylase may be obtained by the screening of a genomic library with a probe, such as a cDNA probe, and isolating those sequences which regulate expression in seed tissue. In this manner, the transcription and translation initiation regions, introns, and/or transcript termination regions of the plant kappa hydroxylase may be obtained for use in a variety of DNA constructs, with or without the kappa hydroxylase structural gene. Thus, nucleic acid sequences corresponding to the plant kappa hydroxylase of this invention may also provide signal sequences useful to direct transport into an organelle 5' upstream non-coding regulatory regions (promoters) having useful tissue and timing profiles, 3' downstream non-coding regulatory region useful as transcriptional and translational regulatory regions and may lend insight into other features of the gene.

Once the desired plant kappa hydroxylase nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant kappa hydroxylase of this invention may be combined with other non-native, or "heterologous", sequences in a variety of ways. By "heterologous" sequences is meant any sequence which is not naturally found joined to the plant kappa hydroxylase, including, for example, combination of nucleic acid sequences from the same plant which are not naturally found joined together.

The DNA sequence encoding a plant kappa hydroxylase of this invention may be employed in conjunction with all or part of the gene sequences normally associated with the kappa hydroxylase. In its component parts, a DNA sequence encoding kappa hydroxylase is combined in a DNA construct having, in the 5' to 3' direction of transcription, a transcription initiation control region capable of promoting transcription and translation in a host cell, the DNA sequence encoding plant kappa hydroxylase and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant kappa hydroxylase foreign to the wild-type cell present therein, for example, by having a recombinant nucleic acid construct encoding a plant kappa hydroxylase therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Saccharomyces cerevisiae*, including genes such as beta-galactosidase, T7 polymerase, tryptophan E and the like.

For the most part, the constructs will involve regulatory regions functional in plants which provide for modified production of plant kappa hydroxylase with resulting modification of the fatty acid composition. The open reading frame, coding for the plant kappa hydroxylase or functional fragment thereof will be joined at its 5' end to a transcription initiation regulatory region such as the wild-type sequence naturally found 5' upstream to the kappa hydroxylase structural gene. Numerous other transcription initiation regions are available which provide for a wide variety of constitutive or regulatable, e.g., inducible, transcription of the structural gene functions.

Among transcriptional initiation regions used for plants are such regions associated with the structural genes such as for nopaline and mannopine synthases, or with napin, soybean β-conglycinin, oleosin, 12S storage protein, the cauliflower mosaic virus 35S promoters and the like. The transcription/translation initiation regions corresponding to such structural genes are found immediately 5' upstream to the respective start codons.

In embodiments wherein the expression of the kappa hydroxylase protein is desired in a plant host, the use of all or part of the complete plant kappa hydroxylase gene is desired; namely all or part of the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, including the sequence encoding the plant kappa hydroxylase of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as transcription initiation control regions from the *B. napus* napin gene, or the *Arabidopsis* 12S storage protein, or soybean β-conglycinin (Bray et al., 1987), or the *L. fendleri* kappa hydroxylase promoter described herein are desired. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant kappa hydroxylase or a convenient transcription termination region derived from a different gene source, for example, the transcript termination region which is naturally associated with the transcript initiation region. Where the transcript termination region is from a different gene source, it will contain at least about 0.5 kb, preferably about 1-3 kb of sequence 3' to the structural gene from which the termination region is derived.

Plant expression or transcription constructs having a plant kappa hydroxylase as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to rapeseed (Canola and high erucic acid varieties), *Crambe, Brassica juncea, Brassica nigra*, meadowfoam, flax, sunflower, safflower, cotton, *Cuphea*, soybean, peanut, coconut and oil palms and corn. An important criterion in the selection of suitable plants for the introduction on the kappa hydroxylase is the presence in the host plant of a suitable substrate for the hydroxylase. Thus, for example, production of ricinoleic acid will be best accomplished in plants that normally have high levels of oleic acid in seed lipids. Similarly, production of lesquerolic acid will best be accomplished in plants that have high levels of icosenoic acid in seed lipids.

Depending on the method for introducing the recombinant constructs into the host cell, other DNA sequences may be required. Importantly, this invention is applicable to dicotyledons and monocotyledons species alike and will be readily applicable to new and/or improved transformation and regulation techniques. The method of transformation is not critical to the current invention; various methods of plant transformation are currently available. As newer methods are available to transform crops, they may be directly applied hereunder. For example, many plant species naturally susceptible to *Agrobacterium* infection may be successfully transformed via tripartite or binary vector methods of *Agrobacterium* mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host-cell.

Normally, included with the DNA construct will be a structural gene having the necessary regulatory regions for expression in a host and providing for selection of transformant cells. The gene may provide for resistance to a cytotoxic agent, e.g., antibiotic, heavy metal, toxin, etc., complementation providing prototropy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, micro-injection, electroporation, infiltration, imbibition, DNA particle bombardment, liposome fusion, DNA bombardment or the like. In many instances, it will be desirable to have the construct bordered on one or both sides of the T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall), the latter being permissible, so long as the vir genes are present in the transformed *Agrobacterium* host. The armed plasmid can give a mixture of normal plant cells and gall.

In some instances where *Agrobacterium* is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., (1980), which is incorporated herein by reference. Included with the expression construct and the T-DNA will be one or more markers, which allow for selection of transformed *Agrobacterium* and transformed plant cells. A number of markers have been developed for use with plant cells, such as resistance to kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

Using Hydroxylase Genes to Alter the Activity of Fatty Acid Desaturases

A widely acknowledged goal of current efforts to improve the nutritional quality of edible plant oils, or to facilitate industrial applications of plant oils, is to alter the level of desaturation of plant storage lipids (Topfer et al., 1995). In particular, in many crop species it is considered desirable to reduce the level of polyunsaturation of storage lipids and to increase the level of oleic acid. The precise amount of the various fatty acids in a particular plant oil varies with the intended application. Thus, it is desirable to have a robust method that will permit genetic manipulation of the level of unsaturation to any desired level.

Substantial progress has recently been made in the isolation of genes encoding plant fatty acid desaturases (reviewed in Topfer et al., 1995). These genes have been introduced into various plant species and used to alter the level of fatty acid unsaturation in one of three ways. First, the genes can be placed under transcriptional control of a strong promoter so that the amount of the corresponding enzyme is increased. In some cases this leads to an increase in the amount of the fatty acid that is the product of the reaction catalyzed by the enzyme. For example, Arondel et al. (1992) increased the amount of linolenic acid (18:3) in tissues of transgenic *Arabidopsis* plants by placing the endoplasmic reticulum-localized fad3 gene under transcriptional control of the strong constitutive cauliflower mosaic virus 35S promoter.

A second method of using cloned genes to alter the level of fatty acid unsaturation is to cause transcription of all or part of a gene in transgenic tissues so that the transcripts have an antisense orientation relative to the normal mode of transcription. This has been used by a number of laboratories to reduce the level of expression of one or more desaturase genes that have significant nucleotide sequence homology to the gene used in the construction of the antisense gene (reviewed in Topfer et al.). For instance, antisense repression of the oleate Δ12-desaturase in transgenic rapeseed resulted in a strong increase in oleic-acid content (cf., Topfer et al., 1995).

A third method for using cloned genes to alter fatty acid desaturation is to exploit the phenomenon of cosuppression or "gene-silencing" (Matzke et al., 1995). Although the mechanisms responsible for gene silencing are not known in any detail, it has frequently been observed that in transgenic plants, expression of an introduced gene leads to inactivation of homologous endogenous genes.

For example, high-level sense expression of the *Arabidopsis* fad8 gene, which encodes a chloroplast-localized Δ15-desaturase, in transgenic *Arabidopsis* plants caused suppression of the endogenous copy of the fad8 gene and the homologous fad7 gene (which encodes an isozyme of the fad8 gene) (Gibson et al., 1994). The fad7 and fad8 genes are only 76% identical at the nucleotide level. At the time of publication, this example represented the most divergent pair of plant genes for which cosuppression had been observed.

In view of previous evidence concerning the relatively high level of nucleotide sequence homology required to obtain cosuppression, it is not obvious to one skilled in the art that sense expression in transgenic plants of the castor fatty acyl hydroxylase of this invention would significantly alter the amount of unsaturation of storage lipids.

However, we have established that fatty acyl hydroxylase genes can be used for this purpose as taught in Example 4 of this invention. Of particular importance, this invention teaches the use of fatty acyl hydroxylase genes to increase the proportion of oleic acid in transgenic plant tissues. The mechanism by which expression of the gene exerts this effect is not known but may be due to one of several possibilities which are elaborated upon in Example 4.

The invention now being generally described, it will be more readily understood by reference to the following examples which are included for purposes of illustration only and are not intended to limit the present invention.

EXAMPLES

In the experimental disclosure which follows, all temperatures are given in degrees centigrade (°), weights are given in grams (g), milligram (mg) or micrograms (µg), concentrations are given as molar (M), millimolar (mM) or micromolar (µM) and all volumes are given in liters (l), microliters (µl) or milliliters (ml), unless otherwise indicated.

Example 1

Production of Novel-Hydroxylated Fatty Acids in *Arabidopsis Thaliana*

Overview

The kappa hydroxylase encoded by the previously described fah12 gene from Castor (U.S. patent application Ser. No. 08/320,982 was used to produce ricinoleic acid, lesquerolic acid, densipolic acid and auricolic acid in transgenic *Arabidopsis* plants. This example specifically discloses the method taught in Example 2 of U.S. patent application Ser. No. 08/320,982.

Production of Transgenic Plants

A variety of methods have been developed to insert a DNA sequence of interest into the genome of a plant host to obtain the transcription and translation of the sequence to effect phenotypic changes. The following methods represent only one of many equivalent means of producing transgenic plants and causing expression of the hydroxylase gene.

*Arabidopsis* plants were transformed, by *Agrobacterium*-mediated transformation, with the kappa hydroxylase encoded by the Castor fah12 gene on binary Ti plasmid pB6. This plasmid was previously used to transform *Nicotiana tabacum* for the production of ricinoleic acid (U.S. patent application Ser. No. 08/320,982).

Inoculums of *Agrobacterium tumefaciens* strain GV3101 containing binary Ti plasmid pB6 were plated on L-broth plates containing, 50 µg/ml kanamycin and incubated for 2 days at 30° C. Single colonies were used to inoculate large liquid cultures (L-broth medium with 50 mg/l rifampicin, 110 mg/l gentamycin and 200 mg/l kanamycin) to be used for the transformation of *Arabidopsis* plants.

*Arabidopsis* plants were transformed by the in planta transformation procedure essentially as described by Bechtold et al., (1993). Cells of *A. tumefaciens* GV3101(pB6) were harvested from liquid cultures by centrifugation, then resuspended in infiltration medium at $OD_{600}$=0.8 (Infiltration medium was Murashige and Skoog macro and micronutrient medium (Sigma Chemical Co., St. Louis, Mo.) containing 10 mg/l 6-benzylaminopurine and 5% glucose). Batches of 12-15 plants were grown for 3 to 4 weeks in natural light at a mean daily temperature of approximately 25° C. in 3.5 inch pots containing soil. The intact plants were immersed in the bacterial suspension then transferred to a vacuum chamber and placed under 600 mm of vacuum produced by a laboratory vacuum pump until tissues appeared uniformly water-soaked (approximately 10 min). The plants were grown at 25° C. under continuous light (100 µmol $m^{-2}$ $s^{-1}$ irradiation in the 400 to 700 nm range) for four weeks. The seeds obtained from all the plants in a pot were harvested as one batch. The seeds were sterilized by sequential treatment for 2 min with ethanol followed by 10 min in a mixture of household bleach (Chlorox), water and Tween-80 (50%, 50%, 0.05%) then rinsed thoroughly with sterile water. The seeds were plated at high density (2000 to 4000 per plate) onto agar-solidified medium in 100 mm petri plates containing ½× Murashige and Skoog salts medium enriched with B5 vitamins (Sigma Chemical Co., St. Louis, Mo.) and containing kanamycin at 50 mg/l. After incubation for 48 h at 4° C. to stimulate germination, seedlings were grown for a period of seven days until transformants were clearly identifiable as healthy green seedlings against a background of chlorotic kanamycin-sensitive seedlings. The transformants were transferred to soil for two weeks before leaf tissue could be used for DNA and lipid analysis. More than 20 transformants were obtained.

DNA was extracted from young leaves from transformants to verify the presence of an intact fah12 gene. The presence of the transgene in a number of the putative transgenic lines was verified by using the polymerase chain reaction to amplify the insert from pB6. The primers used were HF2=GCTCTTTTGTGCGCTCATTC (SEQ ID NO:12) and HR1=CGGTACCAGAAAACGCCTTG (SEQ ID NO:13), which were designed to allow the amplification of a 700 bp fragment. Approximately 100 ng of genomic DNA was added to a solution containing 25 pmol of each primer, 1.5 U Taq polymerase (Boehringer Manheim), 200 uM of dNTPs, 50 mM KCl, 10 mM Tris.Cl (pH 9), 0.1% (v/v) Triton X-100, 1.5 mM $MgCl_2$, 3% (v/v) formamide, to a final volume of 50 µl. Amplifications conditions were: 4 min denaturation step at 94° C., followed by 30 cycles of 92° C. for 1 min, 55° C. for 1 min, 72° C. for 2 min. A final extension step closed the program at 72° C. for 5 min. Transformants could be positively identified after visualization of a characteristic 1 kb amplified fragment on an ethidium bromide stained agarose gel. All transgenic lines tested gave a PCR product of a size consistent with the expected genotype, confirming that the lines were, indeed, transgenic. All further-experiments were done with three representative transgenic lines of the wild type designated as 1-3, 4D, 7-4 and one transgenic line of the fad2 mutant line JB12. The transgenic JB12 line was included in order to test whether the increased accumulation of oleic acid in this mutant would have an effect on the amount of ricinoleic acid that accumulated in the transgenic plants.

Analysis of Transgenic Plants

Leaves and seeds from fah12 transgenic *Arabidopsis* plants were analyzed for the presence of hydroxylated fatty acids using gas chromatography. Lipids were extracted from 100-200 mg leaf tissue or 50 seeds. Fatty acid methyl esters (FAMES) were prepared by placing tissue in 1.5 ml of 1.0 M methanolic HCl (Supelco Co.) in a 13×100 mm glass screw-cap tube capped with a teflon-lined cap and heated to 80° C. for 2 hours. Upon cooling, 1 ml petroleum ether was added and the FAMES removed by aspirating off the ether phase which was then dried under a nitrogen stream in a glass tube. One hundred µl of N,O-bis(Trimethylsilyl) trifluoroacetamide (BSTFA; Pierce Chemical Co) and 200 µl acetonitrile was added to derivatize the hydroxyl groups. The reaction was carried out at 70° C. for 15 min. The products were dried under nitrogen, redissolved in 100 µl chloroform and transferred to a gas chromatograph vial. Two µl of each sample were analyzed on a SP2340 fused silica capillary column (30 m, 0.75 mm ID, 0.20 mm film, Supelco), using a Hewlett-Packard 5890 II series Gas Chromatograph. The samples were not split, the temperature program was 195° C. for 18 min, increased to 230° C. at 25° C./min, held at 230° C. for 5 min then down to 195° C. at 25° C./min., and flame ionization detectors were used.

The chromatographic elution time of methyl esters and O-TMS derivatives of ricinoleic acid, lesquerolic acid and auricolic acid was established by GC-MS of lipid samples from seeds of L. fendleri and comparison to published chromatograms of fatty acids from this species (Carlson et al., 1990). A O-TMS-methyl-ricinoleate standard was prepared from ricinoleic acid obtained from Sigma Chemical Co (St, Louis, Mo.). O-TMS-methyl-lesqueroleate and O-TMS-methyl-ricinoleate standards were prepared from triacylglycerols purified from seeds of L. fendleri. The mass spectrum of O-TMS-methyl-ricinoleate, O-TMS-methyl-densipoleate, O-TMS-methyl-lesqueroleate, and O-TMS-methyl-auricoleate are shown in FIGS. 1A-D, respectively. The structures of the characteristic ions produced during mass spectrometry of these derivatives are shown in FIG. 2.

Figure 1A:
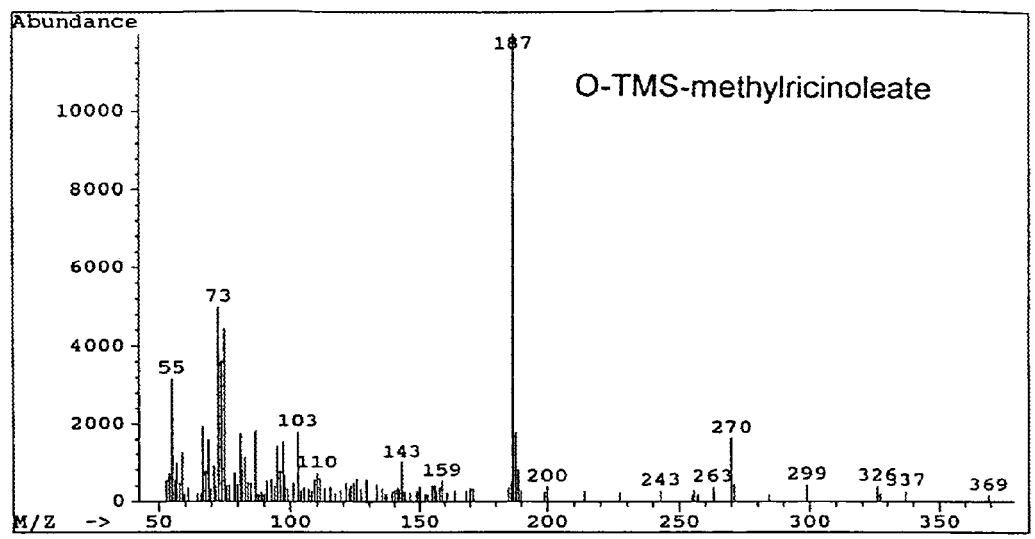
FIGS. 1A-D show the mass spectra of hydroxy fatty acids standards (FIG. 1A, O-TMS-methylricinoleate.
Figure 1B:
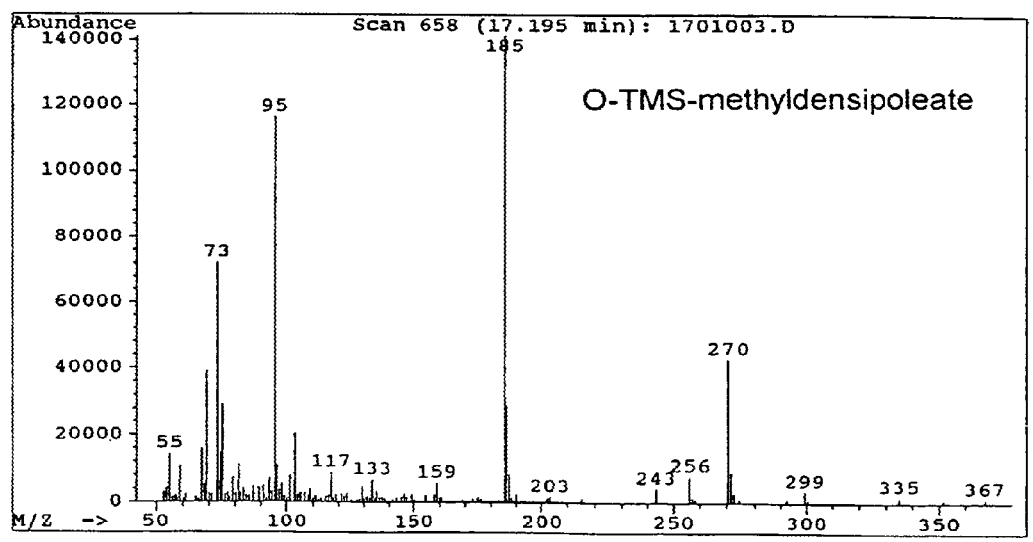
Figure 1C:
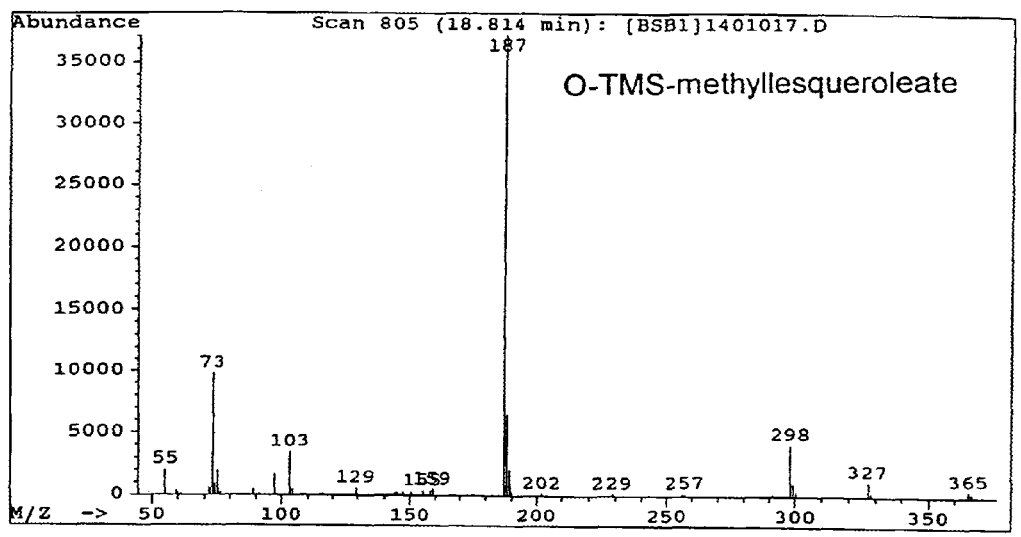
Figure 1D:
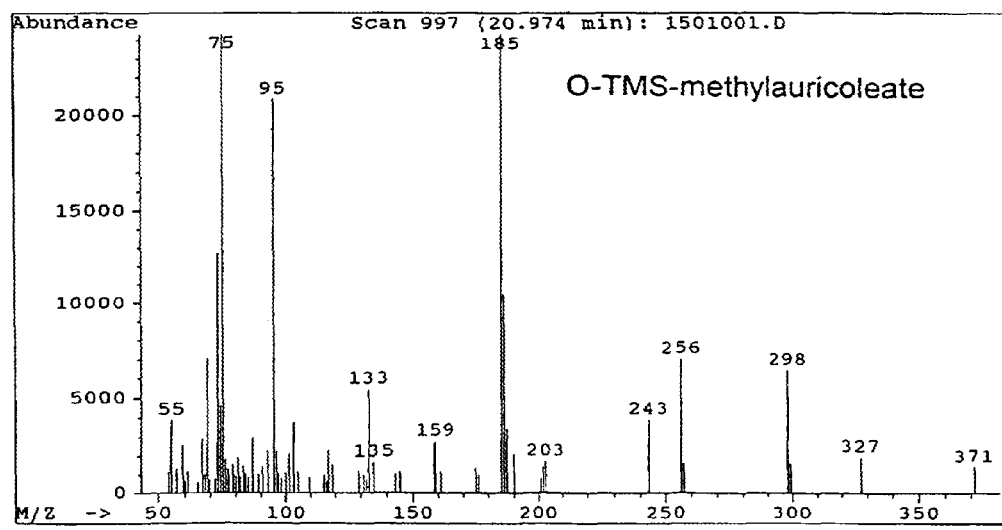
Figure 3:
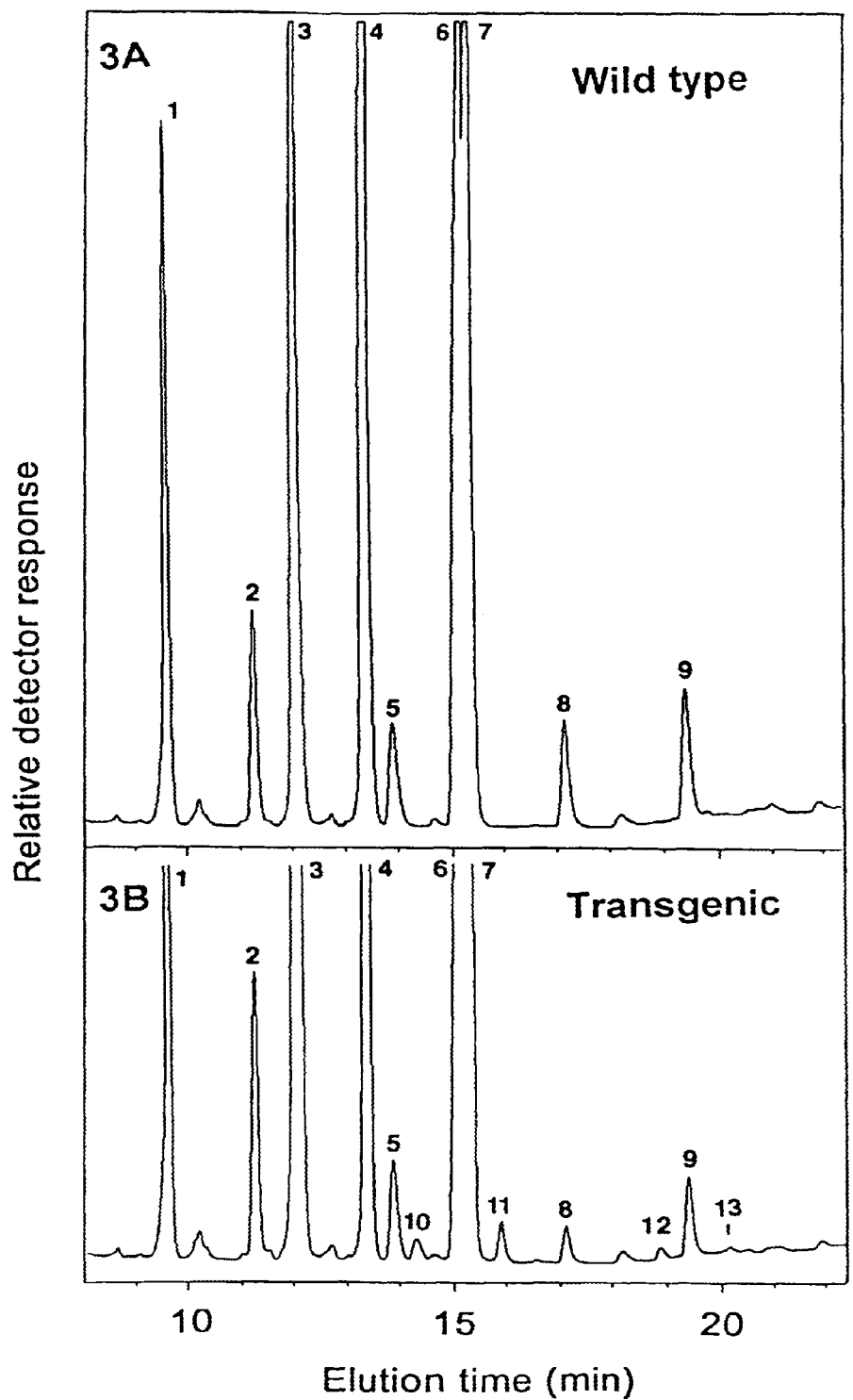
FIG. 3A shows the gas chromatogram of fatty acids extracted from seeds of wild type *Arabidopsis* plants.
FIG. 3B shows the gas chromatogram of fatty acids extracted from seeds of transgenic *Arabidopsis* plants containing the fah12 hydroxylase gene. The numbers indicate the following fatty acids: [1] 16:0; [2] 18:0; [3] 18:1cisΔ9; [4] $18:2^{cis\Delta9,12}$; [5] 20:0; [6] $20:1^{cis\Delta11}$; [7] $18:3^{cis\Delta9,12,15}$; [8] $22:1^{cis\Delta13}$; [9] $24:1^{cis\Delta13}$; [10] ricinoleic acid; [11] densipolic acid; [12] lesquerolic acid; [13] auricolic acid.

Lipid extracted from transgenic tissues were analyzed by gas chromatography and mass spectrometry for the presence of hydroxylated fatty acids. As a matter of reference, the average fatty acid composition of leaves in *Arabidopsis* wild type and fad2 mutant lines was reported by Miquel and Browse (1992). Gas chromatograms of methylated and sylated fatty acids from seeds of wild type and a fah12 transgenic wild type plant are shown in FIGS. 3A and 3B, respectively. The profiles are very similar except for the presence of three small but distinct peaks at 14.3, 15.9 and 18.9 minutes. A very small peak at 20.15 min was also evident. The elution time of the peaks at 14.3 and 18.9 min corresponded precisely to that of comparably prepared ricinoleic and lesquerolic standards, respectively. No significant differences were observed in lipid extracts from leaves or roots of the wild type and the fah12 transgenic wild type lines (Table 1). Thus, in spite of the fact that the fah12 gene is expressed throughout the plant, we observed effects on fatty acid composition only in seed tissue. A similar observation was described previously for transgenic fah12 tobacco in patent application Ser. No. 08/320,982.

with that obtained for the four peaks from the transgenic lines confirms the identity of the four new peaks. On the basis of the three characteristic peaks at M/Z 187, 270 and 299, peak 10 is unambiguously identified as O-TMS-methylricinoleate. On the basis of the three characteristic peaks at M/Z 185, 270 and 299, peak 11 is unambiguously identified as O-TMS-methyldensipoleate. On the basis of the three characteristic peaks at M/Z 187, 298 and 327, peak 12 is unambiguously identified as O-TMS-methyllesqueroleate. On the basis of the three characteristic peaks at M/Z 185, 298 and 327, peak 13 is unambiguously identified as O-TMS-methylauricoleate.

These results unequivocally demonstrate the identity of the fah12 cDNA as encoding a hydroxylase that hydroxylates both oleic acid to produce ricinoleic acid and also hydroxylates icosenoic acid to produce lesquerolic acid. These results also provide additional evidence that the hydroxylase can be functionally expressed in a heterologous plant species in such a way that the enzyme is catalytically functional. These results also demonstrate that expression of this hydroxylase-gene leads to accumulation of ricinoleic, lesquerolic, densipolic and auricolic acids in a plant species that does not normally accumulate hydroxylated fatty acids in extractable lipids.

The presence of lesquerolic acid in the transgenic plants was anticipated in the previous patent application Ser. No. 08/320,982 based on the biochemical evidence suggesting broad substrate specificity of the kappa hydroxylase. By contrast, the accumulation of densipolic and auricolic acids was less predictable. Since *Arabidopsis* does not normally contain significant quantities of the non-hydroxylated precursors of these fatty acids which could serve as substrates for the hydroxylase, it appears that one or more of the three n-3 fatty acid desaturases known in *Arabidopsis* (eg., fad3, fad7, fad8; reviewed in Gibson et al., 1995) are capable of desaturating the hydroxylated compounds at the n-3 position. That is, densipolic acid is produced by the action of an n-3 desaturase

TABLE 1

Fatty acid composition of lipids from transgenic and wild type *Arabidopsis*.

| Fatty acid | Seed | | | | Leaf | | Root | |
|---|---|---|---|---|---|---|---|---|
| | WT | FAH12/WT | FAH12/fad2 | JB12 | WT | FAH12/WT | WT | FAH12/WT |
| 16:0 | 8.5 | 8.2 | 6.4 | 6.1 | 16.5 | 17.5 | 23.9 | 24.9 |
| 16:3 | 0 | 0 | 0 | 0 | 10.1 | 9.8 | 0 | 0 |
| 18:0 | 3.2 | 3.5 | 2.9 | 3.5 | 1.3 | 1.2 | 2.0 | 1.9 |
| 18:1 | 15.4 | 26.3 | 43.4 | 47.8 | 2.4 | 3.4 | 5.4 | 3.2 |
| 18:2 | 27.0 | 21.4 | 10.2 | 7.2 | 15.1 | 14.0 | 32.2 | 29.4 |
| 18:3 | 22.0 | 16.6 | — | 9.7 | 36.7 | 36.0 | 26.7 | 30.6 |
| 20:1 | 14.0 | 14.3 | — | 13.1 | 0 | 0 | 0 | 0 |
| 22:1 | 2.0 | 1.0 | 0.5 | 0.5 | 0 | 0 | 0 | 0 |
| 24:1 | 2.5 | 1.7 | 2.0 | 1.6 | 0 | 0 | 0 | 0 |
| 18:1-OH | 0 | 0.4 | 0.3 | 0 | 0 | 0 | 0 | 0 |
| 18:2-OH | 0 | 0.4 | 0.3 | 0 | 0 | 0 | 0 | 0 |
| 20:1-OH | 0 | 0.2 | 0.1 | 0 | 0 | 0 | 0 | 0 |
| 20:2-OH | 0 | 0.1 | 0.1 | 0 | 0 | 0 | 0 | 0 |

The values are the means obtained from analysis of samples from three independent transgenic lines, or three independent samples of wild type and fad2 lines.

In order to confirm that the observed new peaks in the transgenic lines corresponded to derivatives of ricinoleic, lesquerolic, densipolic and auricolic acids, mass spectrometry was used. The fatty acid derivatives were resolved by gas chromatography as described above except that a Hewlett-Packard 5971 series mass selective detector was used in place of the flame ionization detector used in the previous experiment. The spectra of the four new peaks in FIG. 3B (peak numbers 10, 11, 12 and 13) are shown in FIGS. 4A-D, respectively. Comparison of the spectrum obtained for the standards on ricinoleic acid. Auricolic acid is produced by the action of an n-3 desaturase on lesquerolic acid. Because it is located in the endoplasmic reticulum, the fad3 desaturase is almost certainly responsible. This can be tested in the future by producing fah12-containing transgenic plants of the fad3-deficient mutant of *Arabidopsis* (similar experiments can be done with fad7 and fad8). It is also formally possible that the enzymes that normally elongate $18{:}1^{cis\Delta 9}$ to $20{:}1^{cis\Delta 11}$ may elongate $12OH{-}18{:}1^{cis\Delta 9}$ to $14OH{-}20{:}2^{cis\Delta 11}$, and $12OH{-}18{:}2^{cis\Delta 9,15}$ to $14OH{-}20{:}2^{cis\Delta 11,17}$.

The amount of the various fatty acids in seed, leaf and root lipids of the control and transgenic plants is also presented in Table 1. Although the amount of hydroxylated fatty acids produced in this example is less than desired for commercial production of ricinoleate and other hydroxylated fatty acids from plants, we envision numerous improvements of this invention that will increase the level of accumulation of hydroxylated fatty acids in plants that express the fah12 or related hydroxylase genes. Improvements in the level and tissue specificity of expression of the hydroxylase gene is envisioned. Methods to accomplish this by the use of strong, seed-specific promoters such as the *B. napus* napin promoter or the native promoters of the castor fah12 gene or the corresponding hydroxylase gene from *L. fendleri* will be obvious to one skilled in the art. Additional improvements are envisioned to involve modification of the enzymes which cleave hydroxylated fatty acids from phosphatidylcholine, reduction in the activities of enzymes which degrade hydroxylated fatty acids and replacement of acyltransferases which transfer hydroxylated fatty acids to the sn-1, sn-2 and sn-3 positions of glycerolipids. Although genes for these enzymes have not been described in the scientific literature, their utility in improving the level of production of hydroxylated fatty acids can be readily envisioned based on the results of biochemical investigations of ricinoleate synthesis.

Although *Arabidopsis* is not an economically important plant species, it is widely accepted by plant biologists as a model for higher plants. Therefore, the inclusion of this example is intended to demonstrate the general utility of the invention described here and in the previous application Ser. No. 08/320,982 to the modification of oil composition in higher plants. One advantage of studying the expression of this novel gene in *Arabidopsis* is the existence in this system of a large body of knowledge on lipid metabolism, as well as the availability of a collection of mutants which can be used to provide useful information on the biochemistry of fatty acid hydroxylation in plant species. Another advantage is the ease of transposing any of the information obtained on metabolism of ricinoleate in *Arabidopsis* to closely related species such as the crop plants *Brassica napus*, *Brassica juncea* or *Crambe abyssinica* in order to mass produce ricinoleate, lesqueroleate or other hydroxylated fatty acids for industrial use. The kappa hydroxylase is useful for the production of ricinoleate or lesqueroleate in any plant species that accumulates significant levels of the precursors, oleic acid and icosenoic acid. Of particular interest are genetically modified varieties that accumulate high levels of oleic acid. Such varieties are currently available for sunflower and Canola. Production of lesquerolic acid and related hydroxy fatty acids can be achieved in species that accumulate high levels of icosenoic acid or other long chain monoenoic acids. Such plants may in the future be produced by genetic engineering of plants that do not normally make such precursors. Thus, we envision that the use of the kappa hydroxylase is of general utility.

Example 2

Isolation of *Lesquerella* Kappa Hydroxylase Genomic Clone

Overview

Regions of nucleotide sequence that were conserved in both the Castor kappa hydroxylase and the *Arabidopsis* fad2 Δ12 fatty acid desaturase were used to design oligonucleotide primers. These were used with genomic DNA from *Lesquerella fendleri* to amplify fragments of several homologous genes. These amplified fragments were then used as hybridization probes to identify full length genomic clones from a genomic library of *L. fendleri*.

Hydroxylated fatty acids are specific to the seed tissue of *Lesquerella* sp., and are not found to any appreciable extent in vegetative tissues. One of the two genes identified by this method was expressed in both leaves and developing seeds and is therefore thought to correspond to the Δ12 fatty acid desaturase. The other gene was expressed at high levels in developing seeds but was not expressed or was expressed at very low levels in leaves and is the kappa hydroxylase from this species. The identity of the gene as a fatty acyl hydroxylase was established by functional expression of the gene in yeast.

The identity of this gene will also be established by introducing the gene into transgenic *Arabidopsis* plants and showing that it causes the accumulation of ricinoleic acid, lesquerolic acid, densipolic acid and auricolic acid in seed lipids. The promoter of this gene is also of utility because it is able to direct expression of a gene specifically in developing seeds at a time when storage lipids are accumulating. This promoter is, therefore, of great utility for many applications in the genetic engineering of seeds, particularly in members of the *Brassicacea*.

The various steps involved in this process are described in detail below. Unless otherwise indicated, routine methods for manipulating nucleic acids, bacteria and phage were as described by Sambrook et al. (1989).

Isolation of a Fragment of the *Lesquerella* Kappa Hydroxylase Gene

Oligonucleotide primers for the amplification of the *L. fendleri* kappa hydroxylase were designed by choosing regions of high deduced amino acid sequence homology between the Castor kappa hydroxylase and the *Arabidopsis* Δ12 desaturase (fad2). Because most amino acids are encoded by several different codons, these oligonucleotides were designed to encode all possible codons that could encode the corresponding amino acids.

The sequence of these mixed oligonucleotides was:

```
Oligo 1:  TAYWSNCAYMGNMGNVAYCA      (SEQ ID NO:14)

Oligo 2:  RTGRTGNGCNACRTGNGTRTC    (SEQ ID NO:15)
(Where: Y = C + T; W = A + T; S = G + C; N = A + G + C + T; M
= A + C; R = A + G)
```

These oligonucleotides were used to amplify a fragment of DNA from *L. fendleri* genomic DNA by the polymerase chain reaction (PCR) using the following conditions: Approximately 100 ng of genomic DNA was added to a solution containing 25 pmol of each primer, 1.5 U Taq polymerase (Boehringer Manheim), 200 uM of dNTPs, 50 mM KCl, 10 mM Tris.Cl (pH 9), 0.1% (v/v) Triton X-100, 1.5 mM MgCl$_2$, 3% (v/v) formamide, to a final volume of 50 μl. Amplifications conditions were: 4 min denaturation step at 94° C., followed by 30 cycles of 92° C. for 1 min, 55° C. for 1 min, 72° C. for 2 min. A final extension step closed the program at 72° C. for 5 min.

PCR products of approximately 540 bp were observed following electrophoretic separation of the products of the PCR reaction in agarose gels. Two of these fragments were cloned into pBluescript (Stratagene) to give rise to plasmids pLesq2 and pLesq3. The sequence of the inserts in these two plasmids was determined by the chain termination method. The sequence of the insert in pLesq2 is presented as FIG. 5 (SEQ ID NO:1) and the sequence of the insert in pLesq3 is presented as FIG. 6 (SEQ ID NO:2). The high degree of sequence identity between the two clones indicated that they were both potential candidates to be either a Δ12 desaturase or a gamma hydroxylase.

Northern Analysis

In *L. fendleri*, hydroxylated fatty acids are found in large amounts in seed oils but are not found in appreciable amounts in leaves. An important criterion in discriminating between a fatty acyl desaturase and kappa hydroxylase is that the kappa hydroxylase gene is expected to be expressed more highly in tissues which have high level of hydroxylated fatty acids than in other tissues. In contrast, all plant tissues should contain mRNA for an ω6 fatty acyl desaturase since diunsaturated fatty acids are found in the lipids of all tissues in most or all plants.

Therefore, it was of great interest to determine whether the gene corresponding to pLesq2 was also expressed only in seeds, or is also expressed in other tissues. This question was addressed by testing for hybridization of pLesq2 to RNA purified from developing seeds and from leaves.

Total RNA was purified from developing seeds and young leaves of *L. fendleri* using an Rneasy RNA extraction kit (Qiagen), according to the manufacturer's instructions. RNA concentrations were quantified by UV spectrophotometry at λ=260 and 280 nm. In order to ensure even loading of the gel to be used for Northern blotting, RNA concentrations were further adjusted after recording fluorescence under UV light of RNA samples stained with ethidium bromide and run on a test denaturing gel.

Total RNA prepared as described above from leaves and developing seeds was electrophoresed through an agarose gel containing formaldehyde (Iba et al., 1993). An equal quantity (10 μg) of RNA was loaded in both lanes, and RNA standards (0.16-1.77 kb ladder, Gibco-BRL) were loaded in a third lane. Following electrophoresis, RNA was transferred from the gel to a nylon membrane (Hybond N+, Amersham) and fixed to the filter by exposure to UV light.

A $^{32}$P-labelled probe was prepared from insert DNA of clone pLesq2 by random priming and hybridized to the membrane overnight at 52° C., after it had been prehybridized for 2 h. The prehybridization solution contained 5×SSC, 10×Denhardt's solution, 0.1% SDS, 0.1M KPO$_4$ pH 6.8, 100 μg/ml salmon sperm DNA. The hybridization solution had the same basic composition, but no SDS, and it contained 10% dextran sulfate and 30% formamide. The blot was washed once in 2×SSC, 0.5% SDS at 65° C. then in 1×SSC at the same temperature.

Figure 7:
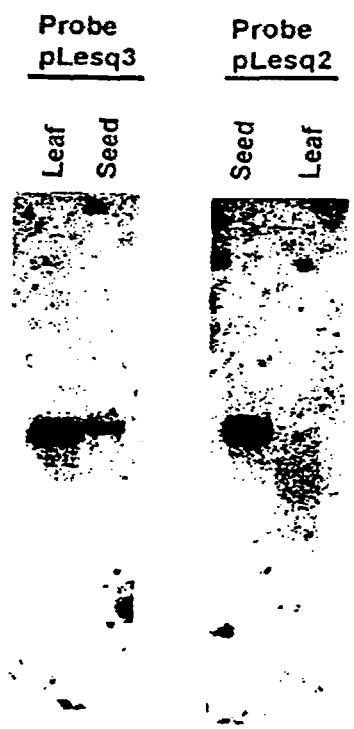
FIG. 7 shows a Northern blot of total RNA from seeds of *L. fendleri* probed with pLesq2 or pLesq3. S, indicates RNA is from seeds; L, indicates RNA is from leaves.

Brief (30 min) exposure of the blot to X-ray film revealed that the probe pLesq2 hybridized to a single band only in the seed RNA lane (FIG. 7). The blot was re-probed with the insert from pLesq3 gene, which gave bands of similar intensity in the seed and leaf lanes (FIG. 7).

These results show that the gene corresponding to the clone pLesq2 is highly and specifically expressed in seed of *L. fendleri*. In conjunction with knowledge of the nucleotide and deduced amino acid sequence, strong seed-specific expression of the gene corresponding to the insert in pLesq2 is a convincing indicator of the role of the enzyme in synthesis of hydroxylated fatty acids in the seed oil.

Characterization of a Genomic Clone of the Gamma Hydroxylase

Genomic DNA was prepared from young leaves of *L. fendleri* as described by Murray and Thompson (1980). A Sau3AI-partial digest genomic library constructed in the vector λDashII (Stratagene, 11011 North Torrey Pines Road, La Jolla Calif. 92037) was prepared by partially digesting 500 μg of DNA, size-selecting the DNA on a sucrose gradient (Sambrook et al., 1989), and ligating the DNA (12 kb average size) to the BamHI-digested arms of λDashII. The entire ligation was packaged according to the manufacturer's conditions and plated on *E. coli* strain XL1-Blue MRA-P2 (Stratagene). This yielded 5×10$^5$ primary recombinant clones. The library was then amplified according to the manufacturer's conditions. A fraction of the genomic library was plated on *E. coli* XL1-Blue and resulting plaques (150,000) were lifted to charged nylon membranes (Hybond N+, Amersham), according to the manufacturer's conditions. DNA was crosslinked to the filters under UV in a Stratalinker (Stratagene).

Several clones carrying genomic sequences corresponding to the *L. fendleri* hydroxylase were isolated by probing the membranes with the insert from pLesq2 that was PCR-amplified with internal primers and labelled with $^{32}$P by random priming. The filters were prehybridized for 2 hours at 65° C. in 7% SDS, 1 mM EDTA, 0.25 M Na$_2$HPO$_4$ (pH 7.2), 1% BSA and hybridized to the probe for 16 hours in the same solution. The filters were sequentially washed at 65° C. in solutions containing 2×SSC, 1×SSC, 0.5×SSC in addition to 0.1% SDS. A 2.6 kb Xba I fragment containing the complete coding sequence for the gamma-hydroxylase and approximately 1 kb of the 5' upstream region was subcloned into the corresponding site of pBluescript KS to produce plasmid pLesq-Hyd and the sequence determined completely using an automatic sequencer by the dideoxy chain termination method. Sequence data was analyzed using the program DNASIS (Hitachi Company).

The sequence of the insert in clone pLesq-Hyd is shown in FIGS. 8A-B. The sequence entails 1855 bp of contiguous DNA sequence (SEQ ID NO:3). The clone encodes a 401 bp 5' untranslated region (i.e., nucleotides preceding the first ATG codon), an 1152 bp open reading frame, and a 302 bp 3' untranslated region. The open reading frame encodes a 384 amino acid protein with a predicted molecular weight of 44,370 (SEQ ID NO:4). The amino terminus lacks features of a typical signal peptide (von Heijne, 1985).

The exact translation-initiation methionine has not been experimentally determined, but on the basis of deduced amino acid sequence homology to the Castor kappa hydroxylase (noted below) is thought to be the methionine encoded by the first ATG codon at nucleotide 402.

Comparison of the pLesq-Hyd deduced amino acid sequence with sequences of membrane-bound desaturases and the castor hydroxylase (FIGS. 9A-B) indicates that pLesq-Hyd is homologous to these genes. This figure shows an alignment of the *L. fendleri* hydroxylase (SEQ ID NO:4) with the castor hydroxylase (van de Loo et al. 1995), the *Arabidopsis* fad2 cDNA which encodes an endoplasmic reticulum-localized Δ12 desaturase (called fad2) (Okuley et al., 1994), two soybean fad2 desaturase clones, a *Brassica napus* fad2 clone, a *Zea mays* fad2 clone and partial sequence of a *R. communis* fad2 clone.

The high degree of sequence homology indicates that the gene products are of similar function. For instance, the overall homology between the *Lesquerella* hydroxylase and the *Arabidopsis* fad2 desaturase was 92.2% similarity and 84.8% identity and the two sequences differed in length by only one amino acid.

Southern Hybridization

Southern analysis was used to examine the copy number of the genes in the *L. fendleri* genome corresponding to the clone pLesq-Hyd. Genomic DNA (5 μg) was digested with EcoR I, Hind III and Xba I and separated on a 0.9% agarose gel. DNA was alkali-blotted to a charged nylon membrane (Hybond N+, Amersham), according to the manufacturer's protocol. The blot was prehybridized for 2 hours at 65° C. in 7% SDS, 1 mM EDTA, 0.25 M Na$_2$HPO$_4$ (pH 7.2), 1% BSA and hybridized to the probe for 16 hours in the same solution with pLesq-Hyd insert PCR-amplified with internal primers and labelled with $^{32}$P by random priming. The filters were sequentially washed at 65° C. in solutions containing 2×SSC, 1×SSC, 0.5×SSC in addition to 0.1% SDS, then exposed to X-ray film.

The probe hybridized with a single band in each digest of *L. fendleri* DNA (FIG. 10), indicating that the gene from which pLesq-Hyd was transcribed is present in a single copy in the *L. fendleri* genome.

Expression of pLesq-Hyd in Transgenic Plants

There are a wide variety of plant promoter sequences which may be used to cause tissue-specific expression of cloned genes in transgenic plants. For instance, the napin promoter and the acyl carrier protein promoters have previously been used in the modification of seed oil composition by expression of an antisense form of a desaturase (Knutson et al. 1992). Similarly, the promoter for the β-subunit of soybean β-conglycinin has been shown to be highly active and to result in tissue-specific expression in transgenic plants of species other than soybean (Bray et al., 1987). Thus, although we describe the use of the *L. fendleri* kappa hydroxylase promoter in the examples described here, other promoters which lead to seed-specific expression may also be employed for the production of modified seed oil composition. Such modifications of the invention described here will be obvious to one skilled in the art.

Constructs for expression of *L. fendleri* kappa hydroxylase in plant cells are prepared as follows: A 13 kb SalI fragment containing the pLesq-Hyg gene was ligated into the XhoI site of binary Ti plasmid vector pSLJ44026 (Jones et al., 1992) (FIG. 11) to produce plasmid pTi-Hyd and transformed into *Agrobacterium tumefaciens* strains GV3101 by electroporation. Strain GV3101 (Koncz and Schell, 1986) contains a disarmed Ti plasmid. Cells for electroporation were prepared as follows. GV3101 was grown in LB medium with reduced NaCl (5 g/l). A 250 ml culture was grown to $OD_{600}$=0.6, then centrifuged at 4000 rpm (Sorvall GS-A rotor) for 15 min. The supernatant was aspirated immediately from the loose pellet, which was gently resuspended in 500 ml ice-cold water. The cells were centrifuged as before, resuspended in 30 ml ice-cold water, transferred to a 30 ml tube and centrifuged at 5000 rpm (Sorvall SS-34 rotor) for 5 min. This was repeated three times, resuspending the cells consecutively in 30 ml ice-cold water, 30 ml ice-cold 10% glycerol, and finally in 0.75 ml ice-cold 10% glycerol. These cells were aliquoted, frozen in liquid nitrogen, and stored at −80° C. Electroporations employed a Biorad Gene pulsar instrument using cold 2 mm-gap cuvettes containing 40 μl cells and 1 μl of DNA in water, at a voltage of 2.5 KV, and 200 Ohms resistance. The electroporated cells were diluted with 1 ml SOC medium (Sambrook et al., 1989, page A2) and incubated at 28° C. for 2-4 h before plating on medium containing kanamycin (50 mg/l).

*Arabidopsis thaliana* can be transformed with the *Agrobacterium* cells containing pTi-Hyd as described in Example 1 above. Similarly, the presence of hydroxylated fatty acids in the transgeneic *Arabidopsis* plants can be demonstrated by the methods described in Example 1 above.

Constitutive Expression of the *L. fendleri* Hydroxylase in Transgenic Plants

A 1.5 kb EcoR I fragment from pLesq-Hyg comprising the entire coding region of the hydroxylase was gel purified, then cloned into the corresponding site of pBluescript KS (Stratagene). Plasmid DNA from a number of recombinant clones was then restricted with Pst I, which should cut only once in the insert and once in the vector polylinker sequence. Release of a 920 bp fragment with Pst I indicated the right orientation of the insert for further manipulations. DNA from one such clone was further restricted with SalI, the 5' overhangs filled-in with the Klenow fragment of DNA polymerase I, then cut with Sac I. The insert fragment was gel purified, and cloned between the Sma I and Sac I sites of pBI121 (Clontech) behind the Cauliflower Mosaic Virus 35S promoter. After checking that the sequence of the junction between insert and vector DNA was appropriate, plasmid DNA from a recombinant clone was used to transform *A. tumefaciens* (GV3101). Kanamycin resistant colonies were then used for in planta transformation of *A. thaliana* as previously described.

DNA was extracted from kanamycin resistant seedlings and used to PCR-amplify selected fragments from the hydroxylase using nested primers. When fragments of the expected size could be amplified, corresponding plants were grown in the greenhouse or on agar plates, and fatty acids extracted from fully expanded leaves, roots and dry seeds. GC-MS analysis was then performed as previously described to characterize the different fatty acid species and detect accumulation of hydroxy fatty acids in transgenic tissues.

Expression of the *Lesquerella* Hydroxylase in Yeast

In order to demonstrate that the cloned *L. fendleri* gene encoded an oleate-12 hydroxylase, the gene was expressed in yeast cells under transcriptional control of an inducible promoter and the yeast cells were examined for the presence of hydroxylated fatty acids by GC-MS.

In a first step, a lambda genomic clone containing the *L. fendleri* hydroxylase gene was cut with EcoRI, and a resulting 1400 bp fragment containing the coding sequence of the hydroxylase gene was subcloned in the EcoRI site of the pBluescript KS vector (Stratagene). This subclone, pLesq-cod, contains the coding region of the *Lesquerella* hydroxylase plus some additional 3' sequence.

In a second step, pLesqcod was cut with HindIII and XbaI, and the insert fragment was cloned into the corresponding sites of the yeast expression vector pYes2 (In Vitrogen; FIG. 12). This subclone, pLesqYes, contains the *L. fendleri* hydroxylase in the sense orientation relative to the 3' side of the Gal1 promoter. This promoter is inducible by the addition of galactose to the growth medium, and is repressed upon addition of glucose. In addition, the vector carries origins of replication allowing the propagation of pLesqYes in both yeast and *E. coli*.

Transformation of *S. cerevisiae* Host Strain CGY2557

Yeast strain CGY2557 (MATα, GAL$^+$, ura3-52, leu2-3, trp1, ade2-1, lys2-1, hiss, can1-100) was grown overnight at 28° C. in YPD liquid medium (10 g yeast extract, 20 g bactopeptone, 20 g dextrose per liter), and an aliquot of the culture was inoculated into 100 ml fresh YPD medium and grown until the $OD_{600}$ of the culture was 1. Cells were then collected by centrifugation and resuspended in about 200 μl of supernatant. 40 μl aliquots of the cell suspension were then mixed with 1-2 μg DNA and electroporated in 2 mm-gap cuvettes using a Biorad Gene Pulser instrument set at 600 V, 200Ω, 25 μF. 160 μl YPD was added and the cells were plated on selective medium containing glucose. Selective medium consisted of 6.7 g yeast nitrogen base (Difco), 0.4 g casamino acids (Difco), 0.02 g adenine sulfate, 0.03 g L-leucine, 0.02 g L-tryptophan, 0.03 g L-lysine-HCl, 0.03 g L-histidine-HCl, 2% glucose, water to 1 liter. Plates were solidified using 1.5% Difco Bacto-agar. Transformant colonies appeared after 3 to 4 days incubation at 28° C.

Expression of the *L. fendleri* Hydroxylase in Yeast

Independent transformant colonies from the previous experiment were used to inoculate 5 ml of selective medium containing either 2% glucose (gene repressed) or 2% galactose (gene induced) as the sole carbon source. Independent colonies of CGY2557 transformed with pYES2 containing no insert were used as controls.

After 2 days of growth at 28° C., an aliquot of the cultures was used to inoculate 5 ml of fresh selective medium. The new culture was placed at 16° C. and grown for 9 days.

Fatty Acid Analysis of Yeast Expressing the *L. fendleri* Hydroxylase

Cells from 2.5 ml of culture were pelleted at 1800 g, and the supernatant was aspirated as completely as possible. Pellets were then dispersed in 1 ml of 1 N methanolic HCl (Supelco, Bellafonte, Pa.). Transmethylation and derivatization of hydroxy fatty acids were performed as described above. After drying under nitrogen, samples were redissolved in 50 μL chloroform before being analyzed by GC-MS. Samples were injected into an SP2330 fused-silica capillary column (30 m×0.25 mm ID, 0.25 μm film thickness, Supelco). The temperature profile was 100-160° C., 25° C./min, 160-230° C., 10° C./min, 230° C., 3 min, 230-100° C., 25° C./min. Flow rate was 0.9 ml/min. Fatty acids were analyzed using a Hewlett-Packard 5971 series Msdetector.

Gas chromatograms of derivatized fatty acid methyl esters from induced cultures of yeast containing pLesqYes contained a novel peak that eluted at 7.6 min (FIG. 13). O-TMS methyl ricinoleate eluted at exactly the same position on control chromatograms. This peak was not present in cultures lacking pLesqYes or in cultures containing pLesqYes grown on glucose (repressing conditions) rather than galactose (inducing conditions). Mass spectrometry of the peak (FIG. 13) revealed that the peak has the same spectrum as O-TMS methyl ricinoleate. Thus, on the basis of chromatographic retention time and mass spectrum, it was concluded that the peak corresponded to O-TMS methyl ricinoleate. The presence of ricinoleate in the transgenic yeast cultures confirms the identity of the gene as a kappa hydroxylase of this invention.

Example 3

Obtaining Other Plant Fatty Acyl Hydroxylases

In a previous patent application, we described the ways in which the castor fah12 sequence could be used to identify other kappa hydroxylases by methods such as PCR and heterologous hybridization. However, because of the high degree of sequence similarity between Δ12 desaturases and kappa hydroxylases, prior art does not teach how to distinguish between the two kinds of enzymes without a functional test such as demonstrating activity in transgenic plants or another suitable host (e.g., transgenic microbial or animal cells). The identification of the *L. fendleri* hydroxylase provided for the development of criteria by which a hydroxylase and a desaturase may be distinguished solely on the basis of deduced amino acid sequence information.

FIGS. 9A-B show a sequence alignment of the castor and *L. fendleri* hydroxylase sequences with the castor hydroxylase sequence and all publicly available sequences for all plant microsomal Δ12 fatty acid desaturases. Of the 384 amino acid residues in the castor hydroxylase sequence, more than 95% are identical to the corresponding residue in at least one of the desaturase sequences. Therefore, none of these residues are responsible for the catalytic differences between the hydroxylase and the desaturases. Of the remaining 16 residues in the castor hydroxylase and 14 residues in the *Lesquerella* hydroxylase, all but six represent instances where the hydroxylase sequence has a conservative substitution compared with one or more of the desaturase sequences, or there is wide variability in the amino acid at that position in the various desaturases. By conservative, we mean that the following amino acids are functionally equivalent: Ser/Thr, Ile/Leu/Val/Met, Asp/Glu. Thus, these structural differences also cannot account for the catalytic differences between the desaturases and hydroxylases. This leaves just six amino acid residues where both the castor hydroxylase and the *Lesquerella* hydroxylase differ from all of the known desaturases and where all of the known microsomal Δ12 desaturases have the identical amino acid residue. These residues occur at positions 69, 111, 155, 226, 304 and 331 of the alignment in FIG. 9. Therefore, these six sites distinguish hydroxylases from desaturases. Based on this analysis, we claim that any enzyme with greater than 60% sequence identity to one of the enzymes listed in FIG. 9 can be classified as a hydroxylase if it differs from the sequence of the desaturases at these six positions. Because of slight differences in the number of residues in a particular protein, the numbering may vary from protein to protein but the intent of the number system will be evident if the protein in question is aligned with the castor hydroxylase using the numbering system shown herein. Thus, in conjunction with the methods for using the *Lesquerella* hydroxylase gene to isolate homologous genes, the structural criterion disclosed here teaches how to isolate and identify plant kappa hydroxylase genes for the purpose of genetically modifying fatty acid composition as disclosed herein and in the previous application Ser. No. 08/320,982.

In considering which of the six substitutions are solely or primarily responsible for the difference in catalytic activity of the hydroxylases of this invention and the desaturases, we consider it likely that the substitution of a Phe for a Tyr at position 226 may be solely responsible for this difference in catalytic activity because of the known participation of tyrosine radicals in enzyme catalysis. Other substitutions, such as the Ala for Ser at position 331 may have effects at modulating the overall rate of the reaction. On this basis we envision creating novel kappa hydroxylases by site directed mutagenesis of Δ12 desaturases. We also envision converting Δ15 desaturases and Δ9 desaturases to hydroxylases by similar use of site-directed mutagenesis.

Example 4

Using Hydroxylases to Alter the Level of Fatty Acid Unsaturation

Evidence that kappa hydroxylases of this invention can be used to alter the level of fatty acid unsaturation was obtained from the analysis of transgenic plants that expressed the castor hydroxylase under control of the Cauliflower mosaic virus promoter. The construction of the plasmids and the production of transgenic *Arabidopsis* plants was described in Example 1 (above). The fatty acid composition of seed lipids from wild type and six transgenic lines (1-2/a, 1-2/b, 1-3/b, 4F, 7E, 7F) is shown in Table 2.

TABLE 2

| Fatty acid composition of lipids from *Arabidopsis* seeds. | | | | | | | |
|---|---|---|---|---|---|---|---|
| Fatty acid | WT | 1-2/a | 1-2/b | 1-3/b | 4F | 7E | 7F |
| 16:0 | 10.3 | 8.6 | 9.5 | 8.4 | 8.1 | 8.4 | 9 |
| 18:0 | 3.5 | 3.8 | 3.9 | 3.3 | 3.5 | 3.8 | 4.2 |
| 18:1 | 14.7 | 33 | 34.5 | 25.5 | 27.5 | 30.5 | 28.5 |
| 18:2 | 32.4 | 16.9 | 21 | 27.5 | 21.1 | 20.1 | 19.8 |
| 18:3 | 13.8 | — | 14.4 | 14.8 | — | — | — |
| 20:0 | 1.3 | 1.6 | 1 | 1.1 | 2.4 | 1.8 | 2 |
| 20:1 | 22.5 | — | 14.1 | 17.5 | — | — | — |

TABLE 2-continued

Fatty acid composition of lipids from *Arabidopsis* seeds.

| Fatty acid | WT | 1-2/a | 1-2/b | 1-3/b | 4F | 7E | 7F |
|---|---|---|---|---|---|---|---|
| 18:3 20:1 * | — | 31.2 | — | — | 32.1 | 30.8 | 30.6 |
| Ricinoleic | 0 | 0.6 | 0 | 0.1 | 0.2 | 0.7 | 0.9 |
| Densipolic | 0 | 0.6 | 0 | 0.1 | 0.2 | 0.5 | 0.6 |
| Lesquerolic | 0 | 0.2 | 0 | 0 | 0.2 | 0.2 | 0.6 |
| Auricolic | 0 | 0.1 | 0 | 0 | 0 | 0.1 | 0.1 |

The asterisk (*) indicates that for some of these samples, the 18:3 and 20:1 peaks overlapped on the gas chromatograph and, therefore, the total amount of these two fatty acids is reported.

The results in Table 2 show that expression of the castor hydroxylase in transgenic *Arabidopsis* plants caused a substantial increase in the amount of oleic acid (18:1) in the seed lipids and an approximately corresponding decrease in the amount of linoleic acid (18:2). The average amount of oleic acid in the six transgenic lines was 29.9% versus 14.7% in the wild type.

The mechanism by which expression of the castor hydroxylase gene causes increased accumulation of oleic acid is not known. An understanding of the mechanism is not required in order to exploit this invention for the directed alteration of plant lipid fatty acid composition. Furthermore, it will be recognized by one skilled in the art that many improvements of this invention may be envisioned. Of particular interest will be the use of other promoters which have high levels of seed-specific expression.

Since hydroxylated fatty acids were not detected in the seed lipids of transgenic line 1-2b, it seems likely that it is not the presence of hydroxylated fatty acids per se that causes the effect of the castor hydroxylase gene on desaturase activity. We speculate that there may be a protein-protein interaction between the hydroxylase and the Δ12-oleate desaturase or another protein required for the overall reaction (eg., cytochrome b5) or for the regulation of desaturase activity. We envision that the interaction between the hydroxylase and this other protein suppresses the activity of the desaturase. For instance, the quaternary structure of the membrane-bound desaturases has not been established. It is possible that these enzymes are active as dimers or as multimeric complexes containing more than two subunits. Thus, if dimers or multimers formed between the desaturase and the hydroxylase, the presence of the hydroxylase in the complex may disrupt the activity of the desaturase. This general hypothesis will be tested directly by the production of transgenic plants in which the hydroxylase enzyme has been rendered inactive by the elimination of one or more of the histidine residues that have been proposed to bind iron molecules required for catalysis. Several of these histidine residues have been shown to be essential for catalysis by site directed mutagenesis (Shanklin et al., 1994). Codons encoding histidine residues in the castor hydroxylase gene described in U.S. patent application Ser. No. 08/320,982 will be changed to alanine residues as described by Shanklin et al. (1994). The modified genes will be introduced into transgenic plants of *Arabidopsis* and possibly other species such as tobacco by the methods described in Example 1 of this application or in Example 1 of the original version of this application (U.S. application Ser. No. 08/320,982).

In order to examine the effect on all tissues, the strong constitutive cauliflower mosaic virus promoter will be used to cause transcription of the modified genes. However, it will be recognized that in order to specifically examine the effect of expression of the mutant gene on seed lipids, a seed-specific promoter such as the *B. napus* napin promoter or the promoter described in Example 2, above, may be used. An expected outcome is that expression of the inactive hydroxylase protein in transgenic plants will inhibit the activity of the endoplasmic reticulum-localized Δ12-desaturase. Maximum inhibition will be obtained by expressing high levels of the mutant protein.

In a further embodiment of this invention, we envision that mutations that inactivate other hydroxylases, such as the *Lesquerella* hydroxylase of this invention, will also be useful for decreasing the amount of endoplasmic reticulum-localized Δ12-desaturase activity in the same way as the castor gene. In a further embodiment of this invention, we also envision that similar mutations of desaturase genes may be used to inactivate endogenous desaturases. Thus, we envision that expression of catalytically inactive fad2 gene from *Arabidopsis* in transgenic *Arabidopsis* will inhibit the activity of the endogenous fad2 gene product.

Similarly, we envision that expression of the catalytically inactive forms of the Δ12-desaturase from *Arabidopsis* or other plants in transgenic soybean in transgenic rapeseed, *Crambe, Brassica juncea*, Canola, flax, sunflower, safflower, cotton, *cuphea*, soybean, peanut, coconut, oil palm and corn will lead to inactivation of endogenous Δ12-desaturase activity in these species. In a further embodiment of this invention we envision that expression of catalytically inactive forms of other desaturases such as the Δ15-desaturases will lead to inactivation of the corresponding desaturases.

Whatever the precise basis for the inhibitory effect of the castor hydroxylase on desaturation, because the castor hydroxylase has very low nucleotide sequence homology (i.e., about 67%) to the *Arabidopsis* fad2 gene (encoding the endoplasmic reticulum-localized Δ12-desaturase) we envision that the inhibitory effect of this gene, which we provisionally call "protein-mediated inhibition" ("protibition"), will have broad utility because it does not depend on a high degree of nucleotide sequence homology between the transgene and the endogenous target gene. In particular, we envision that the castor hydroxylase may be used to inhibit the endoplasmic reticulum-localized Δ12-desaturase activity of all higher plants. Of particular relevance are those species used for oil production. These include but are not limited to rapeseed, *Crambe, Brassica juncea*, Canola, flax, sunflower, safflower, cotton, *cuphea*, soybean, peanut, coconut, oil palm and corn.

CONCLUDING REMARKS

By the above examples, demonstration of critical factors in the production of novel hydroxylated fatty acids by expression of a kappa hydroxylase gene from Castor in transgenic plants is described. In addition, a complete cDNA sequence of the *Lesquerella fendleri* kappa hydroxylase is also provided. A full sequence of the castor hydroxylase is also given with various constructs for use in host cells. Through this invention, one can obtain the amino acid and nucleic acid sequences which encode plant fatty acyl hydroxylases from a variety of sources and for a variety of applications. Also revealed is a novel method by which the level of fatty acid desaturation can be altered in a directed way through the use of genetically altered hydroxylase or desaturase genes.

All publications mentioned in this specification are indicative of the level of skill of those skilled in the art to which this invention pertains. All publications are herein incorporated by reference to the same extent as if each individual publication wasp specifically and individually indicated to be incorporated by reference.

Although the foregoing invention has been described in some detail by way of illustration and example for purposes of clarity of understanding, it will be obvious that certain changes and modifications may be practiced within the scope of the appended claims.

REFERENCES

Arondel, V., B. Lemieux, I. Hwang, S. Gibson, H. Goodman, C. R. Somerville. Map-based cloning of a gene controlling omega-3 fatty acid desaturation in *Arabidopsis*. Science 258, 1353-1355 (1992).

Atsmon, D. (1989) Castor, in *Oil Crops of the World*, Robbelen, G., Downey, K. R., and Ashri, A., Eds., McGraw-Hill, New York, pp. 438-447.

Bechtold, N., Ellis, J. and Pelletier, G. (1993) In Planta *Agrobacterium* mediated gene transfer by infiltration of adult *Arabidopsis thaliana* plants. C.R. Acad. Sci. Paris 316, 1194-1199.

Beltz, G. A., Jacobs, K. A., Eickbuch, T. H., Cherbas, P. T., Kafatos, F. C. (1983) Isolation of multigene families and determination of homologies by filter hybridization methods. Methods in Enzymology 100, 266-285.

Bray, E. A., Naito, S., Pan, N. S., Anderson, E., Dube, P., Beachy, R. N. (1987) Expression of the β-subunit of β-conglycinin in seeds of transgenic plants. Planta 172, 364-370.

Carlson, K. D., Chaudhry, A., Bagby, M. O (1990) Analysis of oil and meal from *lesquerella fendleri* seed. J. Am. Oil Chem. Soc. 67, 438-442.

Ditta, G., Stanfield, S., Corbin, D., Helinski, D. R. (1980) Broad host range DNA cloning system for gram-negative bacteria: Construction of a gene bank of *Rhizobium meliloti*. Proc. Natl. Acad. Sci. USA 77, 7347-7351.

Gibson, S., Arondel, V., Iba, K., Somerville, C. R. (1994) Temperature Regulated Expression of a Gene Encoding a Chloroplast omega-3 Desaturase from *Arabidopsis thaliana*. Plant Physiol. 106, 1615-1621.

Gould, S. J., Subramani, S., Scheffler, I. E. (1989) Use of the DNA polymerase chain reaction for homology probing. Proc. Natl. Acad. Sci. USA 86, 1934-1938.

Hirsinger, F. (1989) New oil crops, in *Oil Crops of the World*, Robbelen, G., Downey, K. R., and Ashri, A., Eds., McGraw-Hill, New York, pp. 518-533.

Howling, D., Morris, L. J., Gurr, M. I., James, A. T. (1972) The specificity of fatty acid desaturases and hydroxylases. The dehydrogenation and hydroxylation of monoenoic acids, Biochim. Biophys. Acta 260, 10.

Huyuh, T. V., Young, R. A., Davis, R. W. (1985) Constructing and screening cDNA libraries in λgt10 and λgt11. In DNA Cloning, Vol. 1: A Practical Approach, (ed) D. M. Glover. IRL Press, Washington D. C. Pp 49-77.

Iba, K., Gibson, S., Nishiuchi, T., Fuse, T., Nishimura, M., Arondel, V., Hugly, S., and Somerville, C. (1993) A gene encoding a chloroplast omega-3 fatty acid desaturase complements alterations in fatty acid desaturation and chloroplast copy number of the fad7 mutant of *Arabidopsis thaliana*. J. Biol. Chem. 268, 24099-24105.

Jones, J. D. G., Shlumukov, L., Carland, F., English, J., Scofield, S., Bishop, G. J., Harrison, K. (1992) Effective vectors for transformation, expression of heterologous genes, and assaying transposon excision in transgenic plants. Transgenic Res. 1, 285-297.

Knutson, D. S., Thompson, G. A., Radke, S. E., Johnson, W. B., Knauf, V. C., Kridl, J. C. (1992) Proc. Natl. Acad. Sci. USA 89, 2624-2628.

Koncz, C., Schell, J. (1986) The promoter of $T_L$-DNA gene 5 controls the tissue-specific expression of chimeric genes carried by a novel type of *Agrobacterium* binary vector. Mol. Gen. Genet. 204, 383-396.

Matzke, M., Matzke, A. J. M. (1995) How and why do plants inactivate homologous (Trans)genes? Plant Physiol. 107, 679-685.

Miguel, M. Browse, J. (1992) *Arabidopsis* mutants deficient in polyunsaturated fatty acid synthesis. J. Biol. Chem. 267, 1502-1509.

Murray, M. G., Thompson, W. F. (1980) Rapid isolation of high molecular weight plant DNA. Nucl. Acid Res. 8, 4321'-4325.

Okuley, J., Lightner, J., Feldman, K., Yadav, N., Lark, E., Browse, J. (1994) *Arabidopsis* FAD2 gene encodes the enzyme that is essential for polyunsaturated lipid. Plant Cell 6, 147-158.

Sambrook, J., Fritsch, E. F., and Maniatis, T., *Molecular Cloning: a Laboratory Manual,* 2nd ed., Cold Spring Harbor Laboratory Press, 1989.

Shanklin, J., Whittle, E., Fox, B. G. (1994) Eight histidine residues are catalytically essential in a membrane-associated iron enzyme, stearoyl-CoA desaturase; and are conserved in alkane hydroxylase and xylene hydroxygenase. Biochemistry 33, 12787-12794.

Smith C. R., Jr. (1985) Unusual seed oils and their fatty acids, in *Fatty Acids*, Pryde E. H., Ed., American Oil Chemists' Society, Champaign, Second edition, pp 29-47.

Töpfer, R., Martini, N., Schell, J. (1995) Modification of plant lipid synthesis. Science 268, 681-686.

van de Loo, F. J., Fox, B. G., Somerville, C. (1993) Unusual fatty acids, in *Lipid Metabolism in Plants*, T. S. Moore Jr., Ed., CRC Press, Boca Raton, pp 91-126.

van de Loo, F. N., Turner, S., Somerville, C. R. (1995) An oleate 12-hydroxylase from castor (*Ricinus communis* L.) is a fatty acyl desaturase homolog. Proc. Natl. Acad. Sci. USA 92, 6743-6747.

von Heijne, G. (1985) Signal sequences. J. Mol. Biol. 184, 99-105.

What is claimed is:

1. A seed of a Brassicaceae plant, wherein oil of the seed comprises ricinoleic acid.

2. A plant comprising the seed of claim 1.

3. The plant of claim 1, wherein the plant is selected from the group consisting of *Brassica napus, Brassica juncea, Brassica nigra* and *Crambe abyssinica.*

4. The plant of claim 2, wherein the plant is selected from the group consisting of *Brassica napus, Brassica juncea, Brassica nigra* and *Crambe abyssinica.*

5. A seed oil obtained from the seed of claim 1, wherein the seed oil comprises ricinoleic acid.

6. A seed oil obtained from seeds of a Brassicaceae plant, wherein the seed oil comprises ricinoleic acid.

7. Oil comprising seed oil from a Brassicaceae plant, wherein the seed oil comprises ricinoleic acid.

8. Oil obtained from the seed of claim 1.

* * * * *